US006900291B2

(12) United States Patent
Holmes et al.

(10) Patent No.: US 6,900,291 B2
(45) Date of Patent: May 31, 2005

(54) DETECTION AND QUANTITATION OF 8-OH-ADENINE USING MONOCLONAL ANTIBODIES

(75) Inventors: Eric H. Holmes, Bothell, WA (US); Thomas G. Greene, Seattle, WA (US)

(73) Assignee: CytoChem, Inc., Seattle, WA (US)

( * ) Notice: Subject to any disclaimer, the term of this patent is extended or adjusted under 35 U.S.C. 154(b) by 20 days.

(21) Appl. No.: 10/375,697

(22) Filed: Feb. 25, 2003

(65) Prior Publication Data

US 2003/0186344 A1 Oct. 2, 2003

Related U.S. Application Data

(63) Continuation of application No. 09/654,005, filed on Aug. 23, 2000, now abandoned, which is a continuation of application No. 09/043,461, filed as application No. PCT/US96/15034 on Mar. 18, 1998, now Pat. No. 6,187,551.
(60) Provisional application No. 60/003,976, filed on Sep. 19, 1995.

(51) Int. Cl.[7] .................................. C12Q 1/68
(52) U.S. Cl. .................... 530/387.1; 530/350; 530/403; 530/388.1; 424/193.1; 435/6; 435/5; 435/7.2; 435/7.1; 435/7.91; 435/7.92
(58) Field of Search ........................... 435/6, 5, 7.2, 25, 435/26, 28, 29, 240.27, 7.1, 7.9, 4, 7.91, 7.92; 530/388.1, 350, 403, 387.1; 424/193.1

(56) References Cited

U.S. PATENT DOCUMENTS

| 4,017,597 A | * | 4/1977 | Reynolds ................... 435/7.92 |
| 4,478,934 A | * | 10/1984 | Sato et al. .................. 435/7.93 |
| 4,701,323 A | * | 10/1987 | Roth et al. ............... 424/193.1 |

(Continued)

FOREIGN PATENT DOCUMENTS

| JP | 3-65650 | * | 2/1991 | .......... G01N/33/53 |
| JP | 3065650 | | 3/1991 | |
| WO | WO 92/15707 A1 | | 9/1992 | |

(Continued)

OTHER PUBLICATIONS

Nicolas, M et al, Ann. Inst. Pasteur/Immunol. 1987, vol. 138, pp. 83–96 "Enzyme Immunoassay fo 2'5' oligoadenylates at the femtomole level." .*

(Continued)

*Primary Examiner*—Lynette R. F. Smith
*Assistant Examiner*—Ginny Allen Portner
(74) *Attorney, Agent, or Firm*—Christensen O'Connor Johnson Kindness PLLC

(57) ABSTRACT

The present invention relates to methods and materials for the detection and quantitation 8-OH-Ade in biological specimens. Specifically, the present invention is directed to a group of highly specific monoclonal antibodies reactive with the modified nucleoside structure 8-OH-Ade, and to various immunoassays for 8-OH-Ade utilizing these monoclonal antibodies. The monoclonal antibodies of the present invention may be used in assays for diagnosing or monitoring the progression of certain types of cancer, in addition to a variety of other diseases associated with mutagenesis resulting from oxidative damage of DNA. Assays utilizing the monoclonal antibodies of the present invention may also be used to analyze or monitor toxicant exposure, such as from environmental sources. The monoclonal antibodies of the present invention were prepared with the immunogen 8-OH-adenosine coupled to keyhole limpet hemocyanin (KLH), not to 8-OH-Ade directly. It is believed that the monoclonal antibodies bind with the base portion of the structure (8-OH-Ade) and not the carbohydrate (ribose) or protein linkage region of the conjugate, because, as demonstrated, conjugates bound to nucleosides other than 8-OH-adenosine were unreactive with these antibodies. Therefore, the antibodies of the present invention can be used to detect and quantitate (by the use of a standard curve) the presence of 8-OH-Ade in biological specimens of DNA. Procedures for such an assay include immobilizing the DNA, denaturing it to disrupt the base-pairing scheme exposing the free base structures, and quantitating the amount of 8-OH-Ade present per amount of DAN in a quantitative immunoassay.

8 Claims, 28 Drawing Sheets-

U.S. PATENT DOCUMENTS

| | | | | | |
|---|---|---|---|---|---|
| 4,824,941 | A | * | 4/1989 | Gordon et al. | 530/403 |
| 4,833,084 | A | * | 5/1989 | Carrico | 530/388.21 |
| 4,923,813 | A | | 5/1990 | Hecht et al. | |
| 5,552,285 | A | | 9/1996 | Frenkel | |
| 5,601,981 | A | * | 2/1997 | Malins | 435/6 |
| 5,605,795 | A | * | 2/1997 | Bronstein | 435/6 |
| 5,665,553 | A | | 9/1997 | Malins | |
| 5,721,341 | A | * | 2/1998 | Molko et al. | 530/387.1 |
| 5,827,645 | A | * | 10/1998 | Sundrehagen | 435/4 |
| 6,063,581 | A | * | 5/2000 | Sundrehagen | 435/7.1 |
| 6,187,551 | B1 | * | 2/2001 | Holmes et al. | 435/7.92 |

FOREIGN PATENT DOCUMENTS

| | | | |
|---|---|---|---|
| WO | WO 93/12258 A1 | | 6/1993 |
| WO | 93/12258 | * | 6/1993 |
| WO | 94/25626 | * | 11/1994 |
| WO | WO 95/07907 A1 | | 3/1995 |
| WO | 95/07907 | * | 3/1995 ......... C07D/413/04 |
| WO | WO 96/38588 A1 | | 12/1996 |

OTHER PUBLICATIONS

Batova, IN et al, Biochemistry and molecular biology international (Australia) Mar. 1993, vol. 29(3), "Base specificity and binding of anti–ss/dsDNA monoclonal antibody Application to the determination of ssDNA" pp. 451–466.*

Johnston, MI et al, Biochemistry, Aug. 13, 1985, vol. 24(17), pp. 4710–4708.*

Cailla, H et al, PNAS, Aug. 1982, vol. 79(15) pp. 4762–4766.*

Adamkiewicz, J., et al., "Monoclonal Antibody–Based Immunoanalytical Methods for Detection of Carcinogen–Modified DNA Components," *IARC Sci. Publ.* 70:403–411, 1986.

Bhimani, R.S., et al., "Inhibition of Oxidative Stress in HeLa Cells by Chemopreventive Agents," *Cancer Research* 53:4528–4533, Oct. 1, 1993.

Catty, D., and C. Raykundalia, "ELISA and Related Enzyme Immunoassays," in D. Catty (ed.), *Antibodies: volume II: A Practical Approach*, IRL Press at Oxford University Press, Oxford, England, 1989, pp. 97–154.

Cho, B.P., and F.E. Evans, "Structure of Oxidatively Damaged Nucleic Acid Adducts. 3. Tautomerism, Ionization and Protonation of 8–Hydroxyadenosine Studied by $^{15}$N NMR Spectroscopy," *Nucleic Acids Research* 19(5):1041–1047, 1991.

Degan, P., et al., "Immunoaffinity Isolation of Urinary 8–Hydroxy- 2'–Deoxyguanosine and 8–Hydroxyguanine and Quantitation of 8–Hydroxy- 2'–Deoxyguanosine in DNA by Polyclonal Antibodies," *Carcinogenesis* 12(5):865–871, May 1991.

Dreher, D., and A.F. Junod, "Role of Oxygen Free Radicals in Cancer Development," *European Journal of Cancer* 32A(1):30–38, 1996.

Halliwell, B., "Free Radicals, Antioxidants, and Human Disease: Curiosity, Cause, or Consequence?" *The Lancet* 344:721–724, Sep. 10, 1994.

Halliwell, B., and M. Dizdaroglu, "Commentary: The Measurement of Oxidative Damage to DNA by HPLC and GC/MS Techniques," *Free Rad Res. Comms.* 16(2):75–87, 1992.

Hussain, S.P., et al., "Oxy–Radical Induced Mutagenesis of Hotspot Codons 248 and 249 of the Human p53 Gene," *Oncogene* 9:2277–2281, 1994.

Ide, H., et al., "Immunochemical Measurement of 8–Hydroxypurines in X–Irradiated DNA," Abstracts, 19th Annual Meetings, UCLA Symposia on Molecular & Cellular Biology, *Journal of Cellular Biochemistry*, Supplement 14A, Jan. 13–28, 1990.

Ide, H., et al., "Antibodies to Oxidative DNA Damage: Characterization of Antibodies to 8–Oxopurines," *Cell Biology and Toxicology* 13:405–417, 1997.

Inagake, M., et al., "Inhibition of 1,2–Dimethylhydrazine–Induced Oxidative DNA Damage by Green Tea Extract in Rat," *Jpn. J. Cancer Res.* 86:1106–1111, Nov. 1995.

Lee, Y.–S., et al., "Identification of 8–Hydroxyguanine Glycosylase Activity in Mammalian Tissues Using 8–Hydroxyguanine Specific Monoclonal Antibody," *Biochemical and Biophysical Research Communications*, 196(3):l545–1551, Nov. 15, 1993.

Loft, S., and H.E. Poulsen, "Cancer Risk and Oxidative DNA Damage in Man," *J. Mol. Med.* 74:297–312, 1996.

MacCubbin, A.E., et al., "$^{32}$P–Postlabeling Assay for Free Radical–Induced DNA Damage: The Formamido Remnant of Thymine," *Free Rad. Res. Comms.* 18(1):17–28, 1993.

Malins, D.C., and R. Haimanot, "4,6–Diamino–5–Formamidopyrimidine, 8–Hydroxyguanine and 8–Hydroxyadenine in DNA From Neoplastic Liver of English Sole Exposed to Carcinogens," *Biochemical and Biophysical Research Communications* 173(2):614–619, Dec. 14, 1990.

Malins, D.C., et al., "The Etiology of Breast Cancer," *Cancer* 71(10):3036–3043, May 15, 1993.

Masuda, M., et al., "An Immunohistochemical Analysis for Cancer of the Esophagus Using Monoclonal Antibodies Specific for Modified Nucleosides," *Cancer* 72(12):3571–3578, Dec. 15, 1993.

Musarrat, J., and A.A. Wani, "Quantitative Immunoanalysis of Promutagenic 8–Hydroxy–2'–Deoxyguanosine in Oxidized DNA," *Carcinogenesis* 15(9):2037–2043, 1994.

Musarrat, J., et al., "Prognostic and Aetiological Relevance of 8–Hydroxyguanosine in Human Breast Carcinogenesis," *European Journal of Cancer* 32A(7):1209–1214, 1996.

Nagashima, M., et al., "8–Hydroxydeoxyguanosine Levels in DNA of Human Breast Cancers Are Not Significantly Different From Those of Non–Cancerous Breast Tissues by the HPLC–ECD Method," *Cancer Letters* 90:157–162, 1995.

Park, E.–M., et al., "Assay of Excised Oxidative DNA Lesions: Isolation of 8– Oxoguanine and Its Nucleoside Derivatives From Biological Fluids With a Monoclonal Antibody Column," *Proc. Natl. Acad Sci. USA* 89:3375–3379, Apr. 1992.

Park, J.–W., et al., "Detection of DNA Adducts by High–Performance Liquid Chromatography With Electrochemical Detection," *Carcinogenesis* 10(5):827–832, 1989.

Shigenaga, M.K., and B.N. Ames, "Assays for 8–Hydroxy–2'–Deoxyguanosine: A Biomarker of In Vivo Oxidative DNA Damage," *Free Radical Biology & Medicine* 10:211–216, 1991.

Shigenaga, M.K., et al., "Urinary 8–Hydroxy–2'–Deoxyguanosine as a Biological Marker of In Vivo Oxidative DNA Damage," *Proc. Natl. Acad. Sci. USA* 86:9697–9701, Dec. 1989.

Shigenaga, M.K., et al, "In Vivo Oxidative DNA Damage: Measurement of 8–Hydroxy–2'–Deoxyguanosine in DNA and Urine by High–Performance Liquid Chromatography With Electrochemical Detection," *Methods in Enzymology* 186:521–530, 1990.

Stollar, B.D., "Immunochemical Analyses of Nucleic Acids," in W.E. Cohn and K. Moldave (eds.), *Prog. Nucleic Acid Res. Mol. Biol. 42*:39–67, 1992.

Strickland, P.T., et al., "Methodologies for Measuring Carcinogen Adducts in Humans," *Cancer Epidemiology, Biomarkers & Prevention* 2:607–619, Nov./Dec. 1993.

Takeuchi, T., et al., "Evaluation of 8–Hydroxydeoxyguanosine, a Typical Oxidative DNA Damage, in Human Leukocytes," *Carcinogenesis* 15(8):1519–1523, 1994.

West, G.J., et al., "Radioimmunoassay of 7,8–Dihydro–8–Oxoadenine (8–Hydroxyadenine)," *Int. J. Radiat. Biol. 42*(5):481–490, 1982.

West, G.J., et al., "Radioimmunoassay of a Thymine Glycol," *Radiation Research 90*:595–608, 1982.

Yarborough, A., et al., "Immunoperoxidase Detection of 8–Hydroxydeoxyguanosine in Aflatoxin $B_1$–Treated Rat Liver and Human Oral Mucosal Cells," *Cancer Research 56*:683–688, Feb. 15, 1996.

Yin, B., et al., "Determination of 8–Hydroxydeoxyguanosine by an Immunoaffinity Chromatography–Monoclonal Antibody–Based ELISA," *Free Rad. Biol. & Med. 18*(6):1023–1032, 1995.

* cited by examiner

DETECTION AND QUANTITATION OF 8-OH-ADENINE USING MONOCLONAL ANTIBODIES

CROSS-REFERENCES TO RELATED APPLICATIONS

This application is a continuation of U.S. patent application Ser. No. 09/645,005, filed Aug. 23, 2000 (now abandoned), which is a continuation of U.S. patent application Ser. No. 09/043,461, filed Mar. 18, 1998 (now U.S. Pat. No. 6,187,551), which was the National Stage of International Application No. PCT/US96/15034, filed Sep. 19, 1996, which claims the benefit of U.S. Provisional Application No. 60/003,976, filed Sep. 19, 1995.

This invention was made with United States government support under National Institutes of Health Grant No. R43 CA67163. The United States government has certain rights in the invention.

FIELD OF THE INVENTION

The present invention relates generally to assays for 8-hydroxyadenine (8-OH-Ade) and, more particularly, to improved immunoassays for the detection and quantitation of 8-OH-Ade in biological specimens. The present invention further relates to new monoclonal antibodies directed against 8-OH-Ade for use in the immunoassays.

BACKGROUND OF THE INVENTION

8-OH-Ade is a modified nucleotide base resulting from single electron oxidation reactions. Steenken, "Purine bases, nucleosides and nucleotides: Aqueous solution redox chemistry and transformation of their radical cations è and OH Adducts," *Chem. Rev.*, Vol. 89, pp. 503–520 (1989). The presence of this oxidized base has been detected in biological specimens in a manner consistent with toxicant exposure and carcinogenesis. Malins et al., "The Etiology of Cancer: hydroxyl radical-induced DNA lesions in histologically normal livers of fish from a population with liver tumors," *Aquat. Toxicol.*, Vol. 20, pp. 123–130 (1991) and Malins et al., "The Etiology of Breast Cancer," *Cancer* Vol. 71, No. 10, pp. 3036–3043 (1993). Previous methods of detecting and quantitating 8-OH-Ade have relied on analysis by high performance liquid chromatography-electrochemical detection (HPLC-ECD) (Shigenaga et al., "Urinary 8-hydroxy-2'-Deoxyguanosine as a Biological Marker of In Vivo Oxidative DNA Damage," *Proc. National. Acad. Sci. USA*, Vol. 86, pp. 9697–9701 (1989)) and gas chromatography-mass-spectrometry with selected ion monitoring (GC-MS/SIM) (Malins et al. (1993)) procedures. Recently, assays utilizing polyclonal antibodies have also been used to detect 8-OH-Ade. West et al., "Radioimmunoassay of 7, 8-dihydro-8-oxoadenine (8-hydroxyadenine)," *Int. J. Radiat. Biol.*, Vol. 42, No. 5, pp. 481–490 (1982). The present invention provides new and improved materials and methods for detecting and quantitating the 8-OH-Ade base structure in a biological specimen comprising a group of highly specific monoclonal antibodies against 8-OH-Ade which may be used in a variety of immunoassays.

Oxygen-free radicals are the primary mediators of cellular free-radical reactions. They are produced in normal or pathological cell metabolism, and as a result of exposure to a variety of exogenous sources of oxidative stress such as tobacco smoke, fatty acids in foods, iron and copper ions, and ethanol. Furthermore, ultraviolet light and ionizing radiation can stimulate the generation of oxygen-free radicals.

Oxygen-free radicals cause constant damage which the body's antioxidant defense systems usually repair so that a dynamic equilibrium is maintained. However, occasionally an overabundance of oxygen free radicals in the body occurs. Oxidative stress refers to the condition in which there is an overproduction of oxygen-free radicals or a deficiency in the antioxidant defense and repair mechanisms. Examples of short-term oxidative stress reactions include ischemia, reperfusion injury, acute inflammation and hyperoxia. Dreher et al., "Role of Oxygen Free Radicals in Cancer Development," *European Journal of Cancer*, Vol. 32A(1), pp. 30–38 (1996).

While short-term oxidative stress does not generally result in severe or debilitating illness, chronic oxidative stress can result in oxidative damage to an organisms DNA, which in turn has been associated with a variety of diseases. It has been established that reactive oxygen species play a significant role in mutagenesis, carcinogenesis and tumor promotion. Bhimani et al., "Inhibition of Oxidative Stress in HeLa Cells by Chemopreventive Agents," *Cancer Research*, Vol. 53, pp. 4528–4533 (1993). The dismutation of superoxide yields hydrogen peroxide, which is highly reactive in vivo. Hydrogen peroxide reacts with partially reduced metal ions to form the hydroxyl radical which can directly inflict DNA damage. Dreher et al. (1996). If hydroxyl radicals are generated close to DNA, they can attack the purine and pyrimidine bases, causing mutations. Halliwell, "Free Radicals, Antioxidants, and Human Disease: Curiosity, Cause, or Consequence?, *The Lancet*, Vol. 344, pp. 721–724 (1994). A discussion of the mechanisms of oxygen-free radical related mutagenesis resulting from DNA damage can be found in Dreher et al., Role of Oxygen-Free Radicals in Cancer Development, *European Journal of Cancer*, Vol. 32A, No. 1, pp. 30–38 (1996).

The involvement of reactive oxygen species in the development of cancer in humans is supported by the abundant presence of oxidative DNA modifications in cancer tissue. Loft et al., "Cancer Risk and Oxidative DNA Damage in Man," *J. Mol. Med.*, Vol.74, pp.297–312 (1996). For example, in breast cancer, base lesion concentrations have been found to be substantial. Base lesions previously reported include 8-OH-Ade, among others. Malins, et al. (1990). It is believed that these base lesions play a pivotal roll in oncogenesis and may further serve as early predictors of breast cancer risk, in addition to a variety of other cancers, due to their inherently mutagenic and carcinogenic effects. See Halliwell (1994) and Bhimani et al. (1993) and Dreher et al. (1996).

Reactive oxygen species have also been implicated in the etiology and pathophysiology of many other human diseases including cardiovascular disease, chronic inflammatory disease, neurodegenerative diseases, rheumatoid arthritis, systemic lupus, erythematosis and sickle cell anemia. Bhimani et al. (1993) and Halliwell (1994).

The etiology of these diseases and their progression, as well as toxicant exposure, can be studied by measuring levels of oxidized DNA bases in biological specimens. Levels of oxidized DNA bases, such as 8-OH-Ade, may also be used as a predictor of risk of disease, thereby allowing preventive intervention before the clinical disease develops. Strickland et al., "Methodologies for Measuring Carcinogen Adducts in Humans," *Cancer Epidemiology, Biomarkers and Prevention*, Vol. 2, pp. 607–619 (1993).

One of the most abundant and most studied oxidative modifications of DNA-bases is the C-8 hydroxylation of guanine. Loft et al., "Cancer Risk and Oxidative DNA Damage in Man", *J. Mol. Med.*, Vol. 74, pp. 297–312 (1996). Other abundant oxidatively modified purines and pyrimidines include 8-oxoadenine, 2-hydroxyadenine, Fapy-A, 5-hydroxy cytosine, and thymine glycol, among others. Loft et al. (1996). Of interest to the present invention in the modified purine 8-OH-Ade.

The presence of oxidative damage in genomic and mitochondrial DNA obtained from biological specimens such as tissues and isolated cells has been studied by a variety of methods, including most commonly gas chromatography/ mass spectroscopy with selective ion monitoring (GC/MS-SIM) and high-performance liquid chromatographic separation (HPLC) followed by detection by UV or electrochemistry. Four primary methods used for monitoring and quantifying oxidative DNA damage in biological specimens are discussed in detail in the review article by Strickland et al. (1993) and include immunoassay techniques, post-labeling, fluorescence spectroscopy and GC/MS.

In view of the great interest in DNA adducts, including 8-OH-Ade, efforts have been made to make antibodies sensitive to these oxidized nucleosides. The use of antibodies to detect DNA adducts began in the mid-1970s. Strickland et al. (1993). A variety of assays utilizing the antibodies have been developed, including the competitive radioimmunoassay, solid phase enzyme immunoassay, competitive solid phase enzyme immunoassay, ELISA, and immunoaffinity chromatography. Strickland et al. (1993). Monoclonal antibodies have been used to detect, for example, 1-methyladenosine and pseudouridine in urine (Matsuda et al., "An Immunohistochemical Analysis for Cancer of the Esophagus Using Monoclonal Antibodies specific for Modified Nucleosides," *Cancer*, Vol. 72, pp. 3571–3578 (1993); various derivatives of guanosine and thymine (Adamkiewicz et al., "Monoclonal Antibody-Based Immunoanalytical Methods for Detection of Carcinogen-Modified DNA Components," *Arc Sc. Publ.*, Vol. 70, pp. 403–41 (1986); and 8-OH-guanine (Lee et al., "Identification of 8-Hydroxyguanine Glycosylase Activity in Mammalian Tissues Using 8-Hydroxyguanine Specific Monoclonal Antibody," *Biochemical and Biophysical Research Communications*, Vol. 196, No. 3, pp. 1545–1551 (1993) and Yin et al., "Determination of 8-Hydroxydeoxyguanosine by an Immunoaffinity Chromatography-Monoclonal Antibody-Base Elisa," *Free Rad. Biol. & Med.*, Vol. 18(6), pp. 1023–1032 (1995)). In the article "Radial Immunoassay of 7, 8-Dihydro-8 Oxoadenine (8-Hydroxyadenine)," West et al. (1982), the authors discuss a specific radioimmunoassay for 8 hydroxy-adenine, and its application in the study of irradiated adenine solutions as well as a preliminary measurements of the production of 8-hydroxyadenine, using polyclonal antibodies.

Although detection and quantitation of oxidized nucleoside basis by immunoassay is gaining popularity, the challenge is in producing a suitable antibody for a specific base. It is preferable to have a specific and highly sensitive antibody which exhibits little cross-reactivity with related molecules. Polyclonal antibodies lack specificity and assays using such antibodies lack sensitivity. Therefore, use of monoclonal antibodies are preferred. However, in practice, obtaining suitable monoclonal antibodies can be difficult. The technique of producing monoclonal antibodies by hybridoma technology is well known in the art. Nevertheless, the results obtained by this technique are unpredictable. Only by carrying out the process for making the monoclonal antibodies can the nature of the, monoclonal antibodies be determined and ascertained. To the bast of the inventors knowledge, no assay has been developed for the detection and quantitation of 8-OH-Ade in a biological specimen using monoclonal antibodies.

Therefore, what is needed in the art is a highly sensitive and specific assay for detecting the presence of and quantitating the amount of 8-OH-Ade present in a biological specimen.

SUMMARY OF THE INVENTION

The present invention relates to methods and materials for the detection and quantitation 8-OH-Ade in biological specimens. Specifically, the present invention is directed to a group of highly specific monoclonal antibodies reactive with the modified nucleoside structure 8-OH-Ade, and to various immunoassays for 8-OH-Ade utilizing these monoclonal antibodies. The monoclonal antibodies of the present invention may be used in assays for diagnosing or monitoring the progression of certain types of cancer, in addition to a variety of other diseases associated with mutagenesis resulting from oxidative damage of DNA. Assays utilizing the monoclonal antibodies of the present invention may also be used to analyze or monitor toxicant exposure, such as from environmental sources. The monoclonal antibodies of the present invention may also be used to detect and quantitate epitopes of 8-OH-Ade.

The monoclonal antibodies of the present invention were prepared with the immunogen 8-OH-adenosine coupled to keyhole limpet hemocyanin (KLH). It is believed that the monoclonal antibodies bind with the base portion of the structure (8-OH-Ade) and not the carbohydrate (ribose) or protein linkage region of the conjugate, because, as demonstrated, conjugates bound to nucleosides other than 8-OH-adenosine were unreactive with these antibodies. Therefore, the antibodies of the present invention can be used to detect and quantitate (by the use of a standard curve) the presence of 8-OH-Ade in biological specimens of DNA. Procedures for such an assay include, for example, immobilizing the DNA, denaturing it to disrupt the base-pairing scheme exposing the free base structures, and quantitating the amount of 8-OH-Ade present per amount of DNA in a quantitative immunoassay.

Thus, it is an object of the present invention to develop an immunoassay for 8-OH-Ade, and its epitopes, in a biological specimen.

It is another object of the present invention to develop monoclonal antibodies specific against 8-OH-Ade.

Yet another object of the present invention is to develop an immunoassay highly sensitive and specific for 8-OH-Ade, utilizing monoclonal antibodies against 8-OH-Ade.

It is a further object of the present invention to prepare antibody producing hybridoma cells characterized by their production of monoclonal antibodies against 8-OH-Ade.

Yet another object of the present is to provide an immunoassay for diagnosing diseases associated with oxidative DNA damage resulting in 8-OH-Ade formation.

It is a further object of the present invention to provide an immunoassay for diagnosing and monitoring the development of cancer in a patient.

Another object of the present invention is to develop an immunoassay for monitoring a patient's response to treatment for diseases associated with oxidative DNA damage resulting in 8-OH-Ade formation.

A further object of the present invention is to develop an immunoassay for monitoring the effects of toxicant exposure in a human or animal.

It is also an object of the present invention to develop an immunoassay for detecting toxicant exposure in a human or animal.

Other aspects and advantages of the present invention will be apparent upon consideration of the following detailed description.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1A is a total ion chromatogram of the trimethylsilated derivative. The major peak eluted at 9.7 min from an HP-1 GC column. FIG. 1B is a mass spectrum of the major peak eluting at 9.7 min. The major ions at m/z 352 and 367, characteristic of 8-OH-Ade, appear in mass spectrum.

DETAILED DESCRIPTION OF THE INVENTION

As used herein, the term "8-OH-Ade" refers to both bound, e.g., incorporated into DNA or RNA, and free forms of the nucleotide base.

The present invention is directed to materials and methods for detecting 8-OH-Ade in a sample of nucleic acids obtained from a biological specimen using monoclonal antibodies. In one aspect of the present invention, monoclonal antibodies are provided that are characterized by their specific reactivity with 8-OH-Ade. Representative embodiments of this aspect of the invention are the monoclonal antibodies identified below, produced by the hybridomas also identified below:

TABLE I

Monoclonal Antibodies of the Present Invention

| Antibody | Hybridoma | Accession No. |
| --- | --- | --- |
| 8A1 | 8A1 | |
| 8A2 | 8A2 | |
| 8A3.E10 | 8A3.E10 | |
| 8A3.E11 | 8A3.E11 | |
| 8A4.B7 | 8A4.B7 | |
| 8A4.G10 | 8A4.G10 | |
| 8A5 | 8A5 | |
| 8A6 | 8A6 | ATCCHB12189 |
| 8A7 | 8A7 | |
| 8A8 | 8A8 | |
| 8A9 | 8A9 | ATCCHB12188 |

The hybridoma cells 8A6 and 8A9 were deposited with American Type Culture Collection located at 12301 Parklawn Drive, Rockville, Md. 20852 on Sep. 13, 1996 and assigned the accession numbers indicated above.

The preferred monoclonal antibodies for use in the assays of the present invention are antibodies 8A6 and 8A9, identified above. . Antibody 8A5 is reactive primarily with 8-OH-Ade, but was also identified as reactive with 8-OH-guanine. Thus, antibody 8A5 may be useful in detecting 8-OH-adducts of purines generally.

Figure 1A:
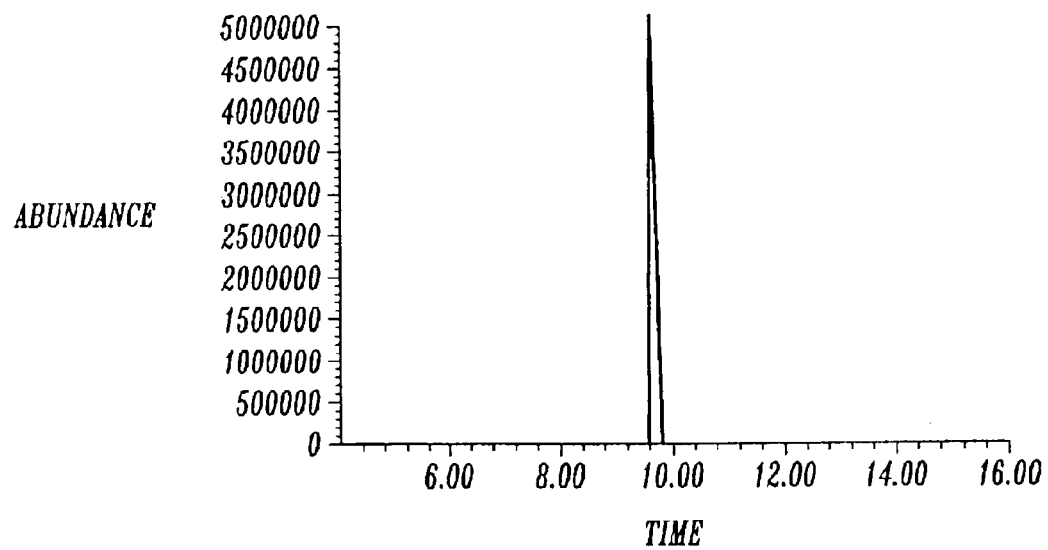
FIGS. 1A and 1B are graphs showing the GC-MS/SIM analysis of synthetic 8-OH-adenosine after hydrolysis using 60% formic acid and triethylsilation.
Figure 1B:
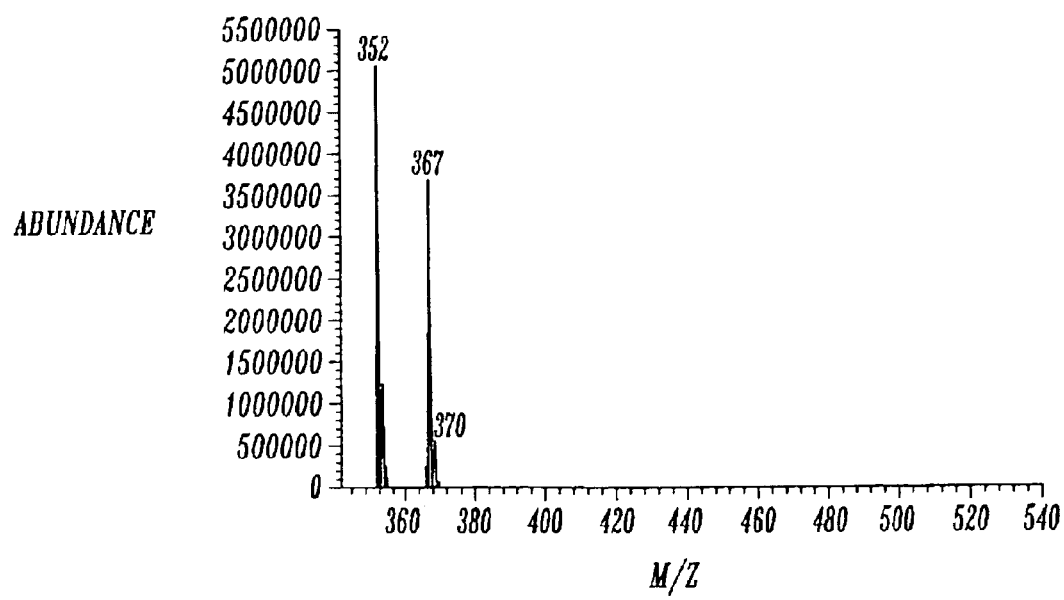
Figure 2:
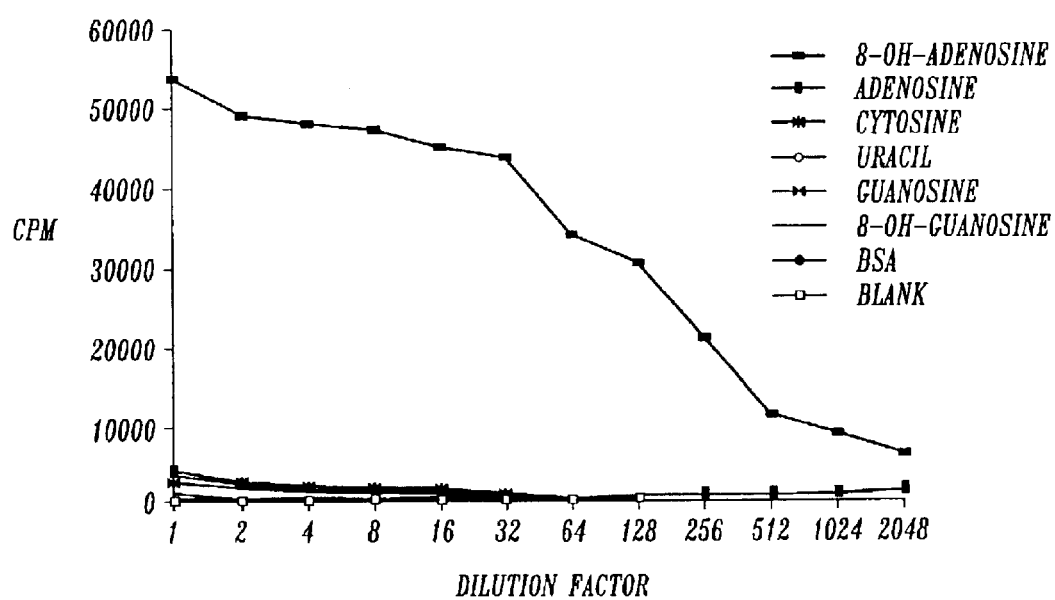
FIG. 2 is a graph of the results of a solid phase immunoassay of antibody binding specificity by analysis of antibody binding to periodate oxidized nucleosides conjugated to BSA for the monoclonal antibody 8A1 of the present invention. The conditions of the assay were as described in Example 4. The protein conjugates were coated onto the plastic surface in 50 µl of volume at a starting concentration of 50 µl/ml and serially diluted 1:2 as indicated. The haptens conjugated to BSA were as indicated in the FIGURE legend.
Figure 3:
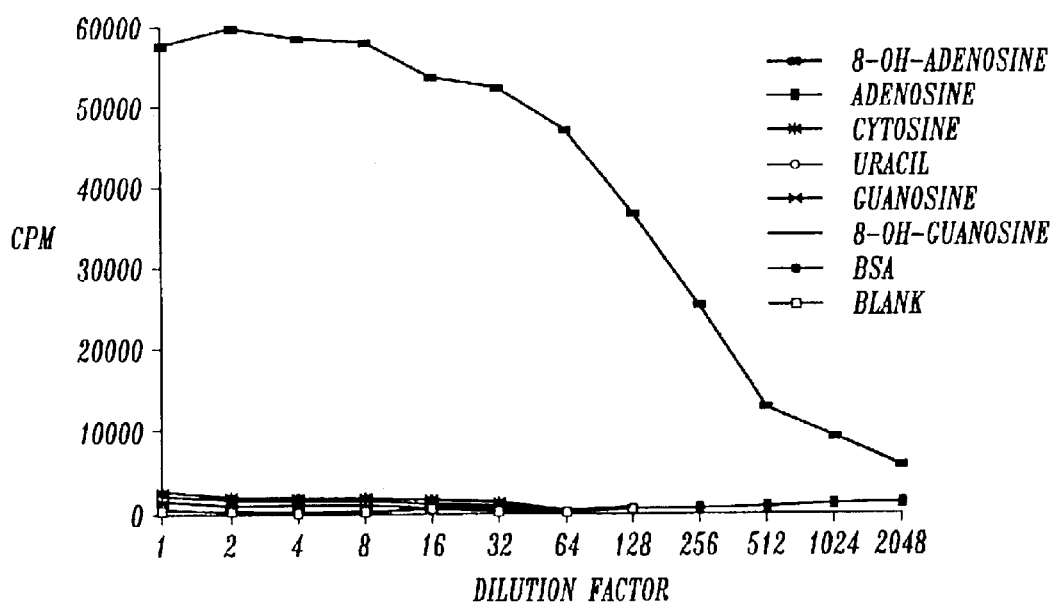
FIG. 3 is a graph of the results of a solid phase immunoassay of antibody binding specificity by analysis of antibody binding to periodate oxidized nucleosides conjugated to BSA for the monoclonal antibody 8A2 of the present invention. The conditions of the assay were as described in Example 4. The protein conjugates were coated onto the plastic surface in 50 µl of volume at a starting concentration of 50 µl/ml and serially diluted 1:2 as indicated. The haptens conjugated to BSA were as indicated in the FIGURE legend.
Figure 4:
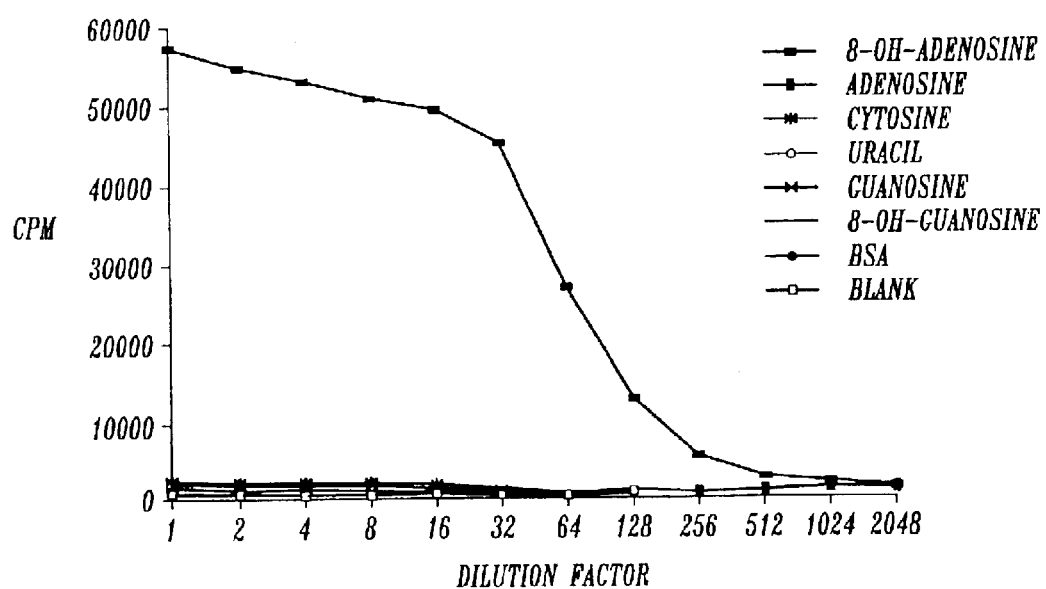
FIG. 4 is a graph of the results of a solid phase immunoassay of antibody binding specificity by analysis of antibody binding to periodate oxidized nucleosides conjugated to BSA for the monoclonal antibody 8A3.E10 of the present invention. The conditions of the assay were as described in Example 4. The protein conjugates, were coated onto the plastic surface in 50 µl of volume at a starting concentration of 50 µg/ml and serially diluted 1:2 as indicated. The haptens conjugated to BSA were as indicated in the FIGURE legend.
Figure 5:
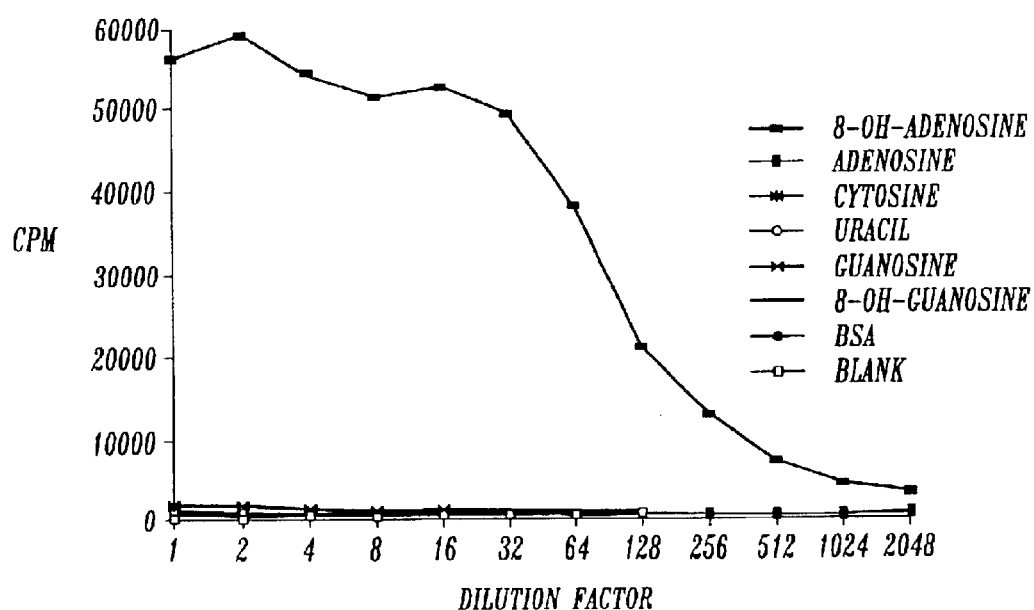
FIG. 5 is a graph of the results of a solid phase immunoassay of antibody binding specificity by analysis of antibody binding to periodate oxidized nucleosides conjugated to BSA for the monoclonal antibody 8A3.E11 of the present invention. The conditions of the assay were as described in Example 4. The protein conjugates were coated onto the plastic surface in 50 µl of volume at a starting concentration of 50 µg/ml and serially diluted 1:2 as indicated. The haptens conjugated to BSA were as indicated in the FIGURE legend.
Figure 6:
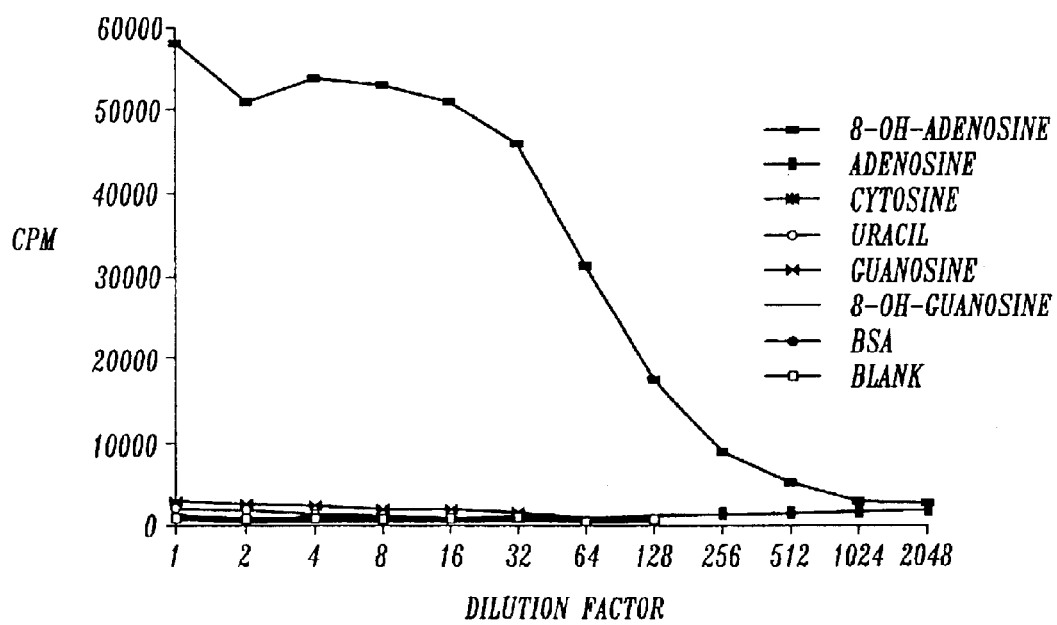
FIG. 6 is a graph of the results of a solid phase immunoassay of antibody binding specificity by analysis of antibody binding to periodate oxidized nucleosides conjugated to BSA for the monoclonal antibody 8A4.B7 of the present invention. The conditions of the assay were as described in Example 4. The protein conjugates were coated onto the plastic surface in 50 µl of volume at a starting concentration of 50 µg/ml and serially diluted 1:2 as indicated. The haptens conjugated to BSA were as indicated in the FIGURE legend.
Figure 7:
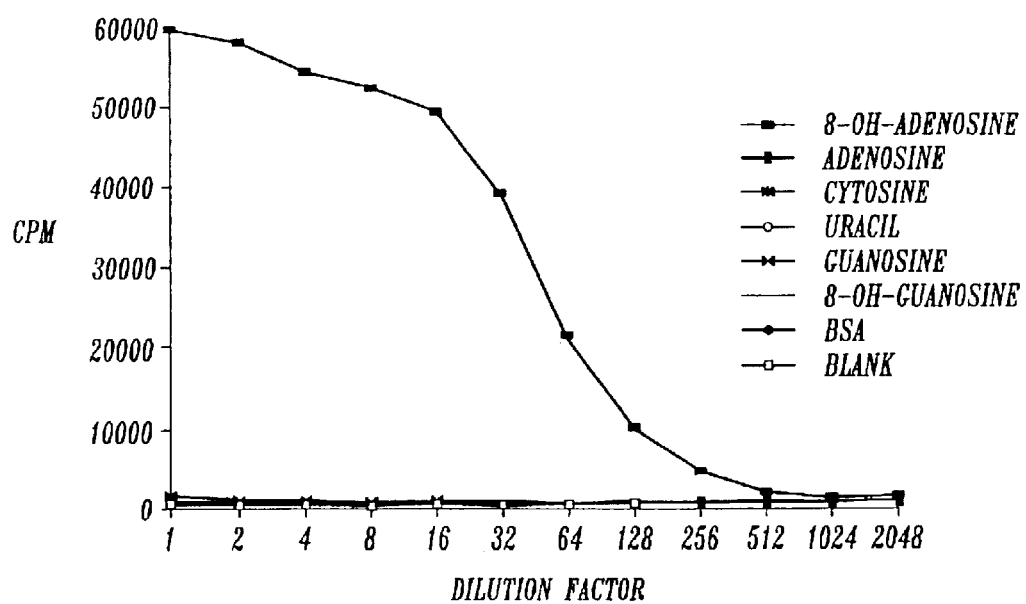
FIG. 7 is a graph of the results of a solid phase immunoassay of antibody binding specificity by analysis of antibody binding to periodate oxidized nucleosides conjugated to BSA for the monoclonal antibody 8A4.G10 of the present invention. The conditions of the assay were as described in Example 4. The protein conjugates were coated onto the plastic surface in 50 µl of volume at a starting concentration of 50 µg/ml and serially diluted 1:2 as indicated. The haptens conjugated to BSA were as indicated in the FIGURE legend.
Figure 8:
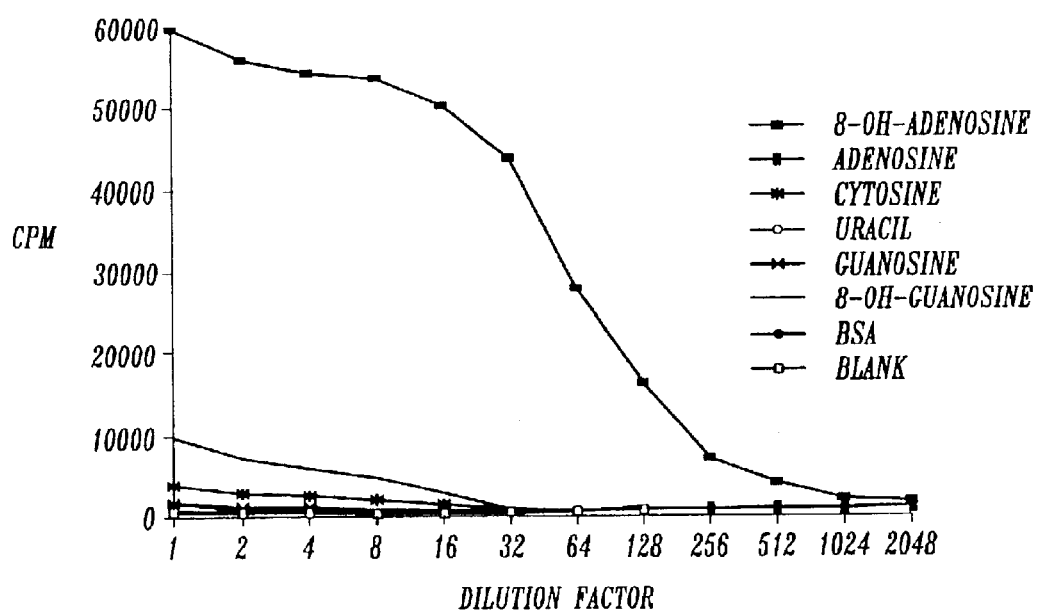
FIG. 8 is a graph of the results of a solid phase immunoassay of antibody binding specificity by analysis of antibody binding to periodate oxidized nucleosides conjugated to BSA for the monoclonal antibody 8A5 of the present invention. The conditions of the assay were as described in Example 4. The protein conjugates were coated onto the plastic surface in 50 µl of volume at a starting concentration of 50 µg/ml and serially diluted 1:2 as indicated. The haptens conjugated to BSA were as indicated in the FIGURE legend.
Figure 9:
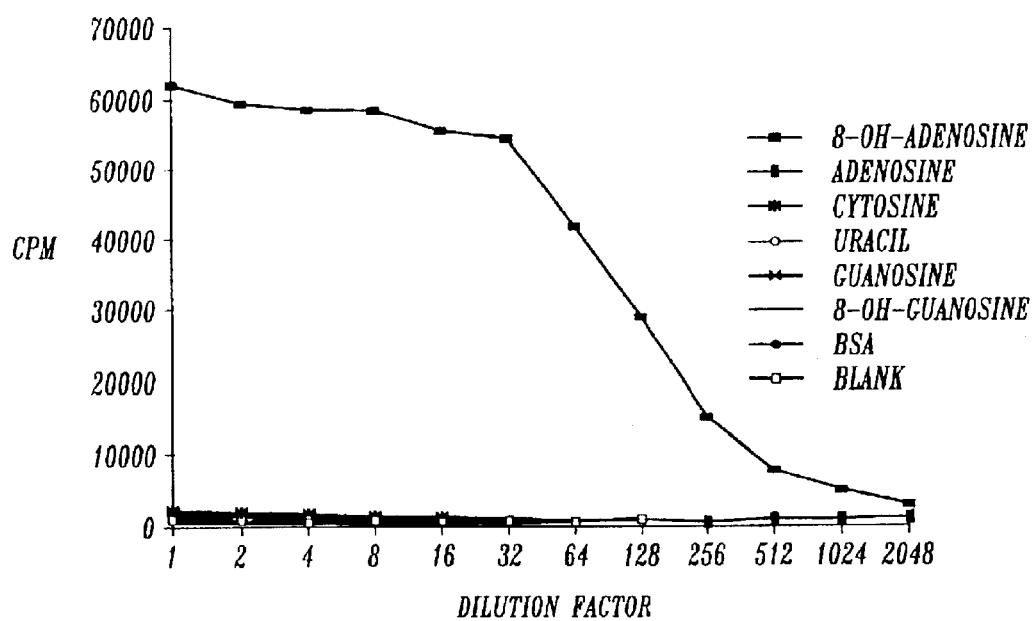
FIG. 9 is a graph of the results of a solid phase immunoassay of antibody binding specificity by analysis of antibody binding to periodate oxidized nucleosides conjugated to BSA for monoclonal antibody 8A6 of the present invention. The conditions of the assay were as described in Example 4. The protein conjugates were coated onto the plastic surface in 50 µl of volume at a starting concentration of 50 µg/ml and serially diluted 1:2 as indicated. The haptens conjugated to BSA were as indicated in the FIGURE legend.
Figure 10:
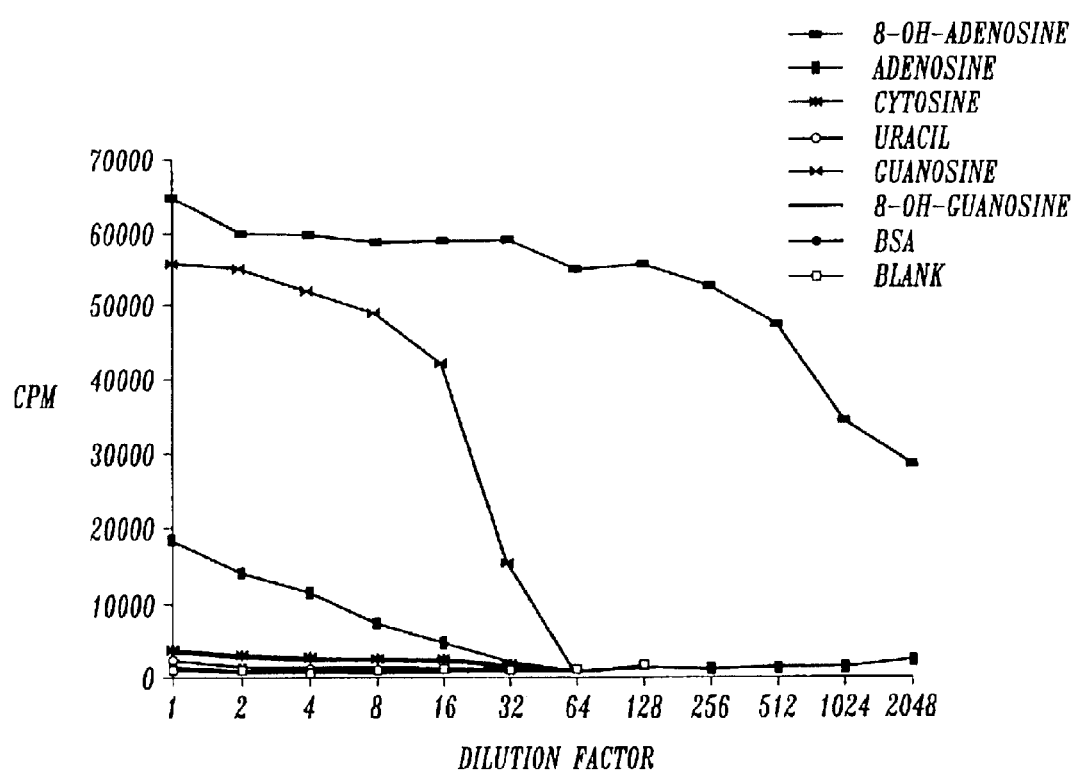
FIG. 10 is a graph of the results of a solid phase immunoassay of antibody binding specificity by analysis of antibody binding to periodate oxidized nucleosides conjugated to BSA for the monoclonal antibody 8A7 of the present invention. The conditions of the assay were as described in Example 4. The protein conjugates were coated onto the plastic surface in 50 µl of volume at a starting concentration of 50 µg/ml and serially diluted 1:2 as indicated. The haptens conjugated to BSA were as indicated in the FIGURE legend.
Figure 11:
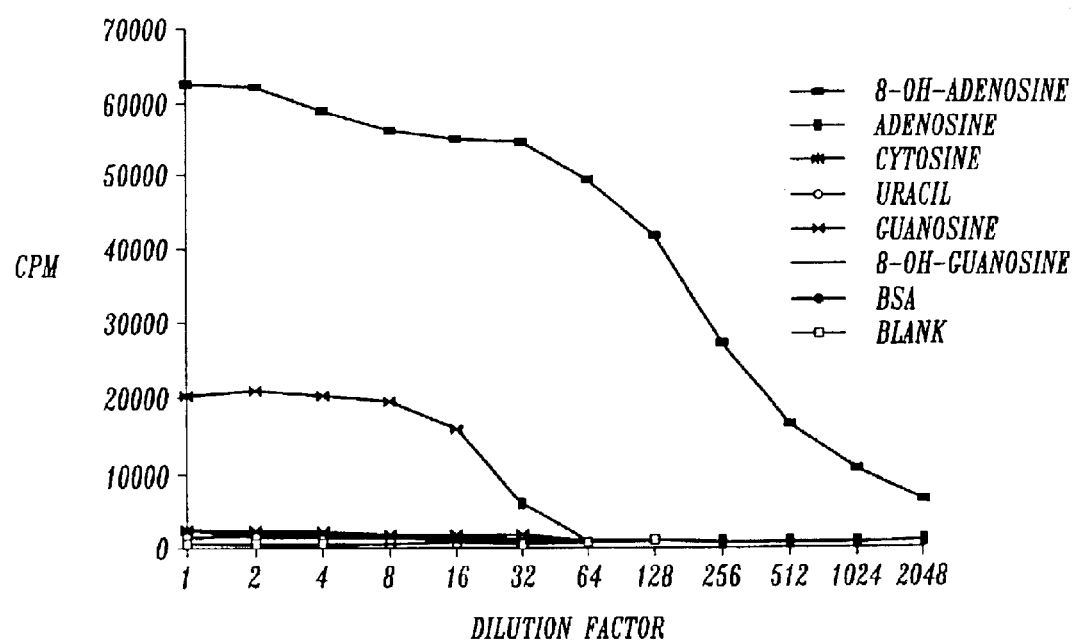
FIG. 11 is a graph of the results of a solid phase immunoassay of antibody binding specificity by analysis of antibody binding to periodate oxidized nucleosides conjugated to BSA for the monoclonal antibody 8A8 of the present invention. The conditions of the assay were as described in Example 4. The protein conjugates were coated onto the plastic surface in 50 µl of volume at a starting concentration of 50 µg/ml and serially diluted 1:2 as indicated. The haptens conjugated to BSA were as indicated in the FIGURE legend.
Figure 12:
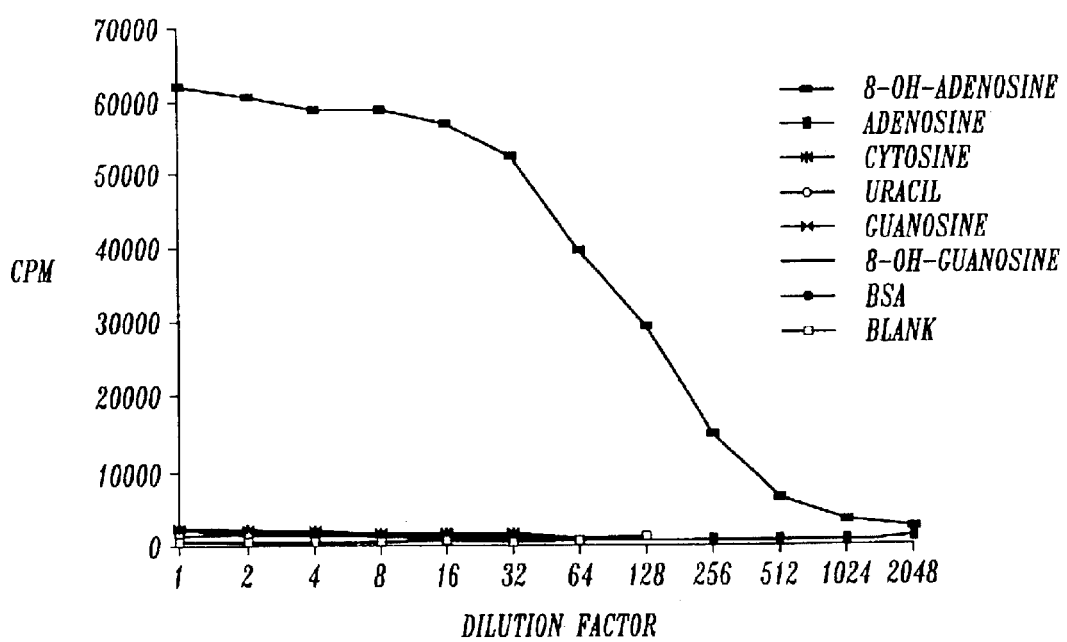
FIG. 12 is a graph of the results of a solid phase immunoassay of antibody binding specificity by analysis of antibody binding to periodate oxidized nucleosides conjugated to BSA for the monoclonal antibody 8A9. The conditions of the assay were as described in Example 4. The protein conjugates were coated onto the plastic surface in 50 µl of volume at a starting concentration of 50 µg/ml and serially diluted 1:2 as indicated. The haptens conjugated to BSA were as indicated in the FIGURE legend.
Figure 13:
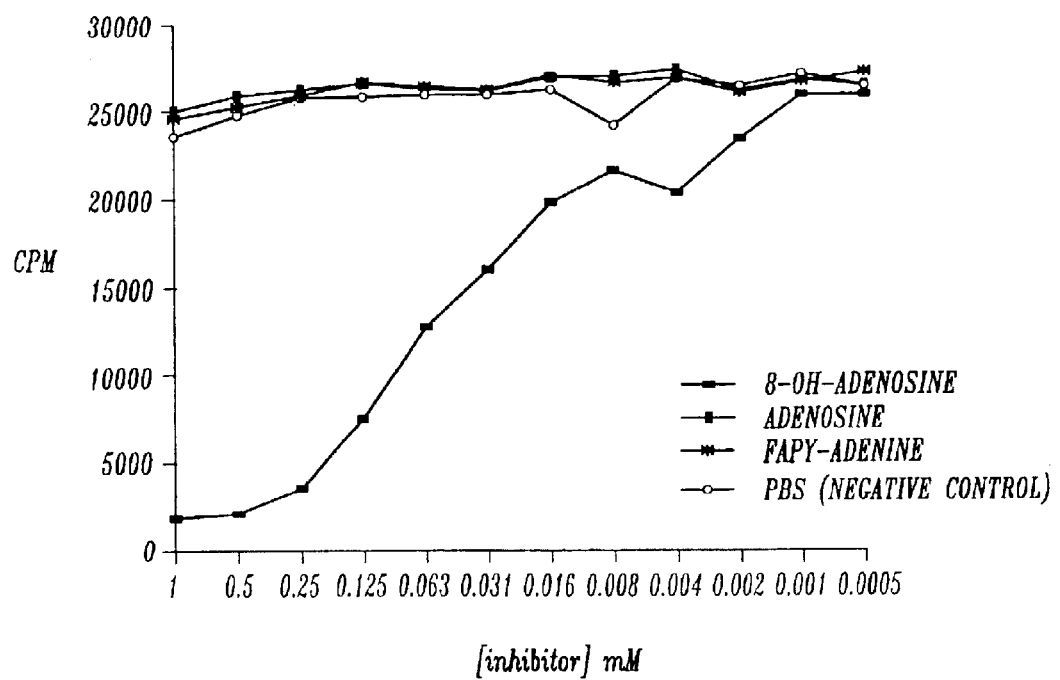
FIG. 13 is a graph showing inhibition of antibody binding to 8-OH-adenosine-BSA conjugates by soluble ligands for the monoclonal antibody 8A1 of the present invention. The data shows results of inhibition of antibody binding to 8-OH-adenosine conjugated BSA (50 µl of 50 µg of protein/ml as coating mixture) in a solid phase assay using commercial 8-OH-AMP (Sigma, St. Louis, Mo.) (prepared from 3',5'cyclic 8-OH-ANT after hydrolysis by nucleotidase), AMP, or 4,6-diamino-5-formamidopyromidine (Fapy-A) as shown in the FIGURE legend. The antibody present in culture supernatant was incubated in the presence of the indicated final concentration of soluble inhibitor overnight prior to the solid phase assay.
Figure 14:
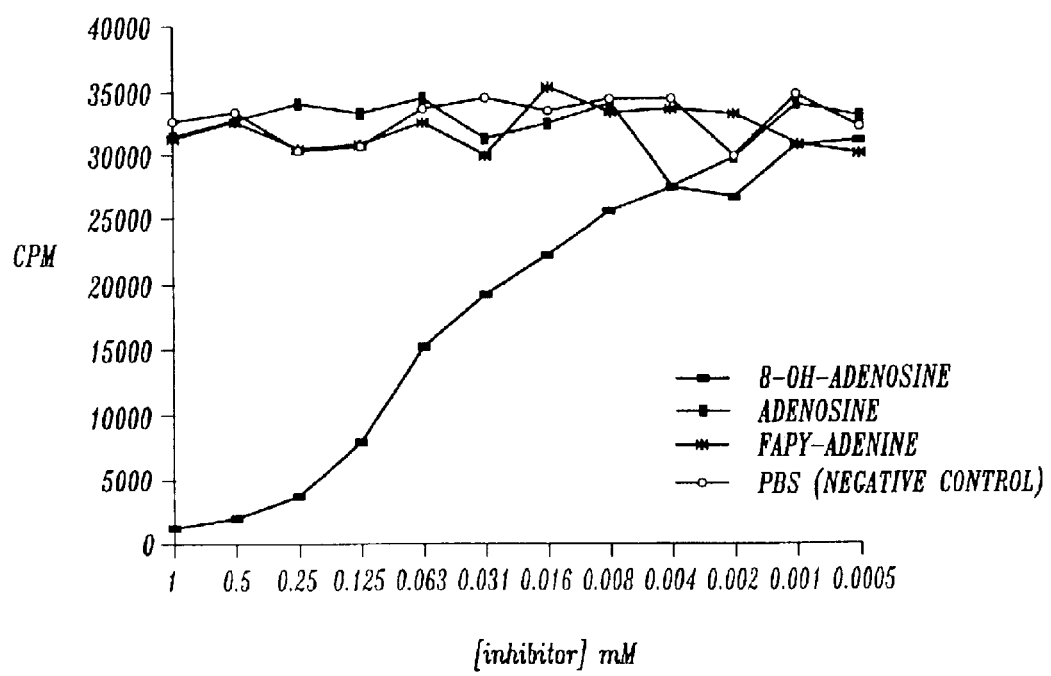
FIG. 14 is a graph showing inhibition of antibody binding to 8-OH-adenosine-BSA conjugates by soluble ligands for the monoclonal antibody 8A2 of the present invention. The data shows results of inhibition of antibody binding to 8-OH-adenosine conjugated BSA (50 µl of 50 µg of protein/ml as coating mixture) in a solid phase assay using commercial 8-OH-AMP (Sigma, St. Louis, Mo.) (prepared from 3',5'cyclic 8-OH-AMP after hydrolysis by nucleotidase), AMP, or 4,6-diamino-5-formamidopyrimidine (Fapy-A) as shown in the FIGURE legend. The antibody present in culture supernatant was incubated in the presence of the indicated final concentration of soluble inhibitor overnight prior to the solid phase assay.
Figure 15:
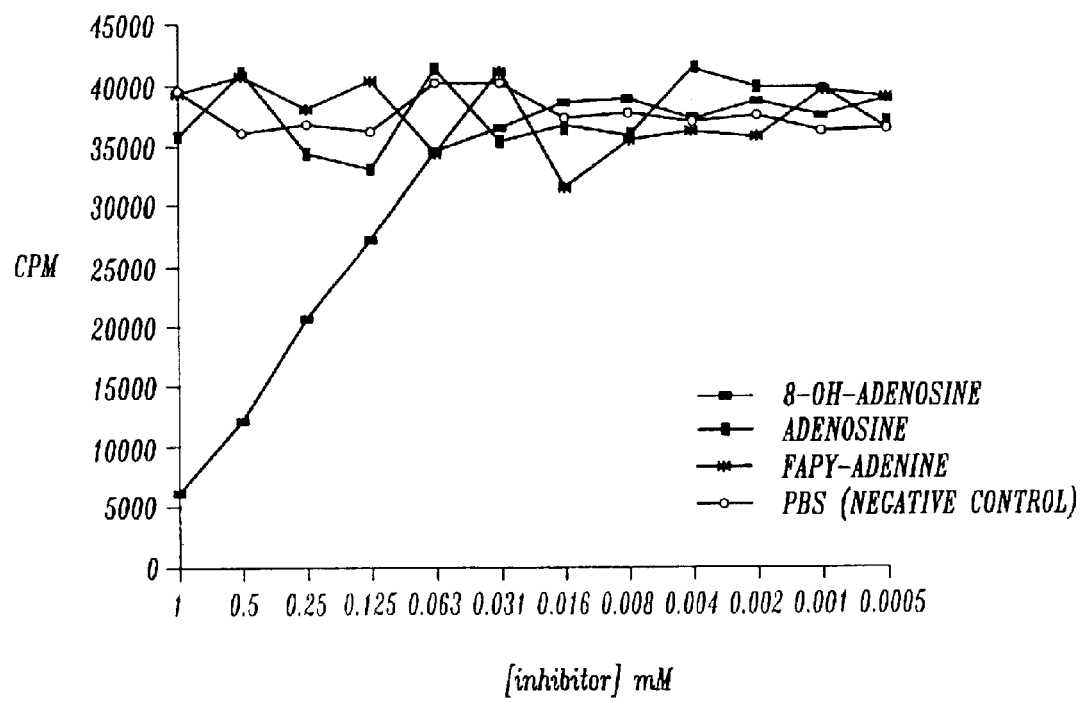
FIG. 15 is a graph showing inhibition of antibody binding to 8-OH-adenosine-BSA conjugates by soluble ligands for the monoclonal antibody 8A3.E10 of the present invention. The data shows results of inhibition of antibody binding to 8-OH-adenosine conjugated BSA (50 µl of 50 µg of protein/ml as coating mixture) in a solid phase assay using commercial 8-OH-AMP (Sigma, St. Louis, Mo.) (prepared from 3',5'cyclic 8-OH-AMP after hydrolysis by nucleotidase), AMP, or 4,6-diamino-5-formamidopyrimidine (Fapy-A) as shown in the FIGURE legend. The antibody present in culture supernatant was incubated in the presence of the indicated final concentration of soluble inhibitor overnight prior to the solid phase assay.
Figure 16:
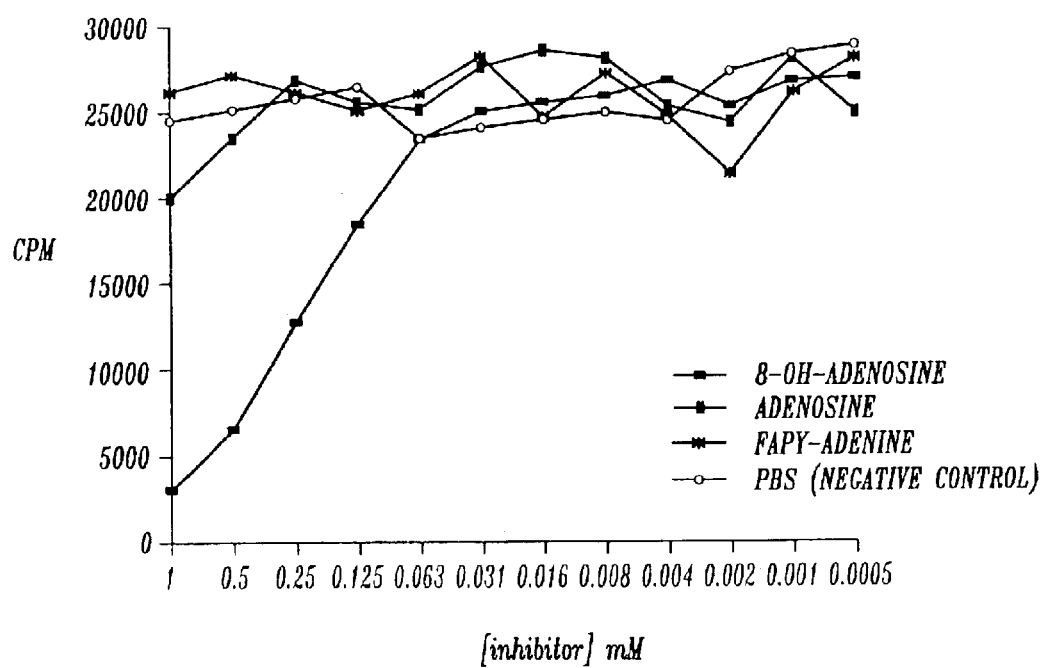
FIG. 16 is a graph showing inhibition of antibody binding to 8-OH-adenosine-BSA conjugates by soluble ligands for the monoclonal antibody 8A3.E11. The data shows results of inhibition of antibody binding to 8-OH-adenosine conjugated BSA (50 µl of 50 µg of protein/ml as coating mixture) in a solid phase assay using commercial 8-OH-AMP (Sigma, St. Louis, Mo.) (prepared from 3',5'cyclic 8-OH-AMP after hydrolysis by nucleotidase), AMP, or 4,6-diamino-5-formamidopyrimidine (Fapy-A) as shown in the FIGURE legend. The antibody present in culture supernatant was incubated in the presence of the indicated final concentration of soluble inhibitor overnight prior to the solid phase assay.
Figure 17:
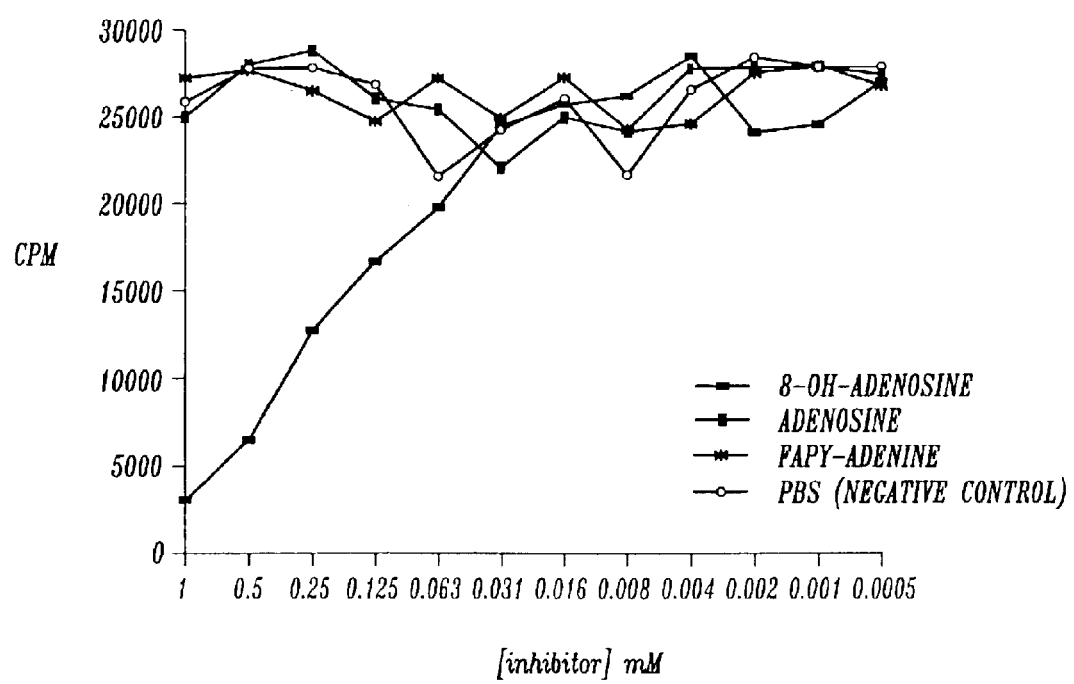
FIG. 17 is a graph showing inhibition of antibody binding to 8-OH-adenosine-BSA conjugates by soluble ligands for the monoclonal antibody 8A4.B7 of the present invention. The data shows results of inhibition of antibody binding to 8-OH-adenosine conjugated BSA (50 µl of 50 µg of protein/ml as coating mixture) in a solid phase assay using commercial 8-OH-AMP (Sigma, St. Louis, Mo.) (prepared from 3',5'cyclic 8-OH-AMP after hydrolysis by nucleotidase), AMP, or 4,6-diamino-5-formamidopyrimidine (Fapy-A) as shown in the FIGURE legend. The antibody present in culture supernatant was incubated in the presence of the indicated final concentration of soluble inhibitor overnight prior to the solid phase assay.
Figure 18:
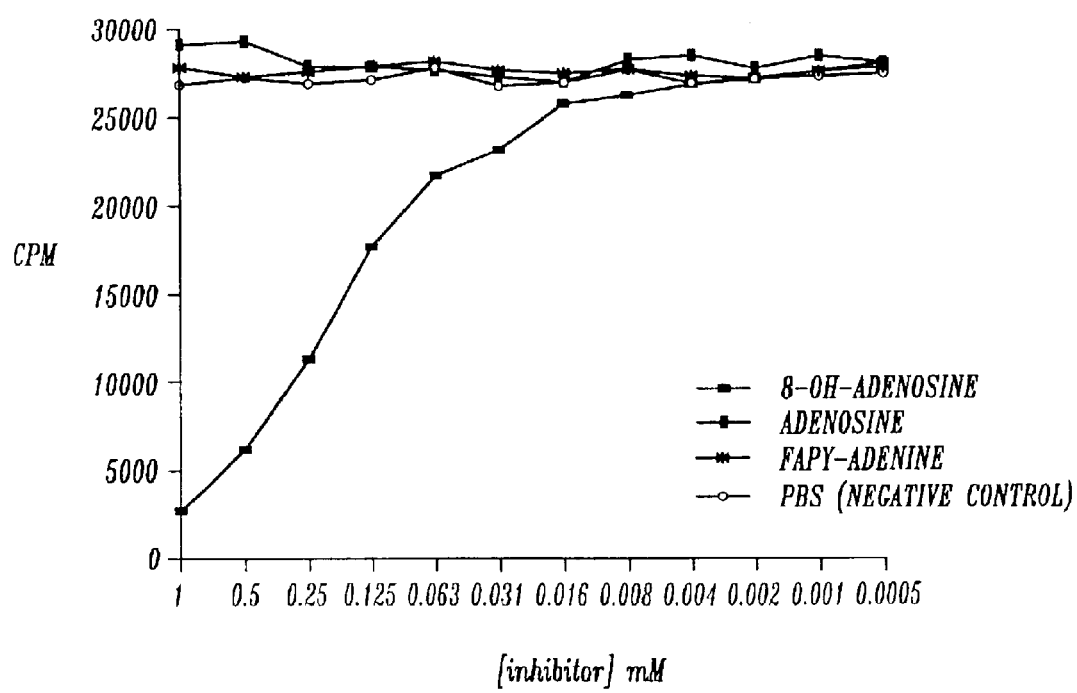
FIG. 18 is a graph showing inhibition of antibody binding to 8-OH-adenosine-BSA conjugates by soluble ligands for the monoclonal antibody 8A4.G10 of the present invention. The data shows results of inhibition of antibody binding to 8-OH-adenosine conjugated BSA (50 µl of 50 µg of protein/ml as coating mixture) in a solid phase assay using commercial 8-OH-AMP (Sigma, St. Louis, Mo.) (prepared from 3',5'cyclic 8-OH-AMP after hydrolysis by nucleotidase), AMP, or 4,6-diamino-5-formamidopyrimidine (Fapy-A) as shown in the FIGURE legend. The antibody present in culture supernatant was incubated in the presence of the indicated final concentration of soluble inhibitor overnight prior to the solid phase assay.
Figure 19:
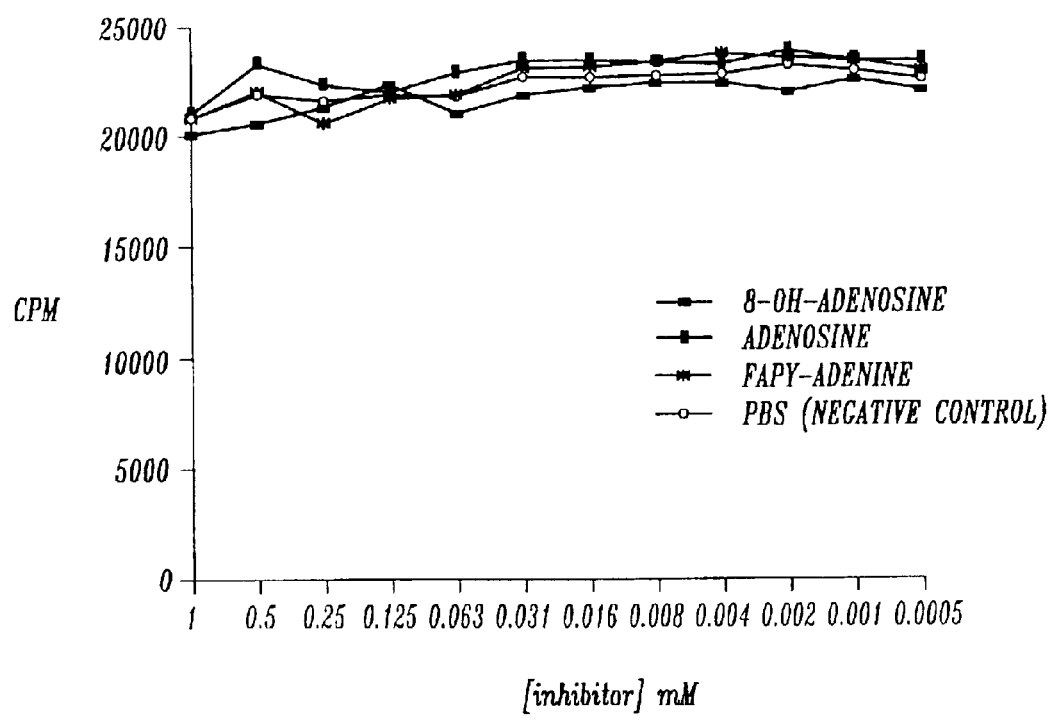
FIG. 19 is a graph showing inhibition of antibody binding to 8-OH-adenosine-BSA conjugates by soluble ligands for monoclonal antibody 8A5 of the present invention. The data shows results of inhibition of antibody binding to 8-OH-adenosine conjugated BSA (50 µl of 50 µg of protein/ml as coating mixture) in a solid phase assay using commercial 8-OH-AMP (Sigma, St. Louis, Mo.) (prepared from 3',5'cyclic 8-OH-AMP after hydrolysis by nucleotidase), AMP, or 4,6-diamino-5-formamidopyrimidine (Fapy-A) as shown in the FIGURE legend. The antibody present in culture supernatant was incubated in the presence of the indicated final concentration of soluble inhibitor overnight prior to the solid phase assay.
Figure 20:
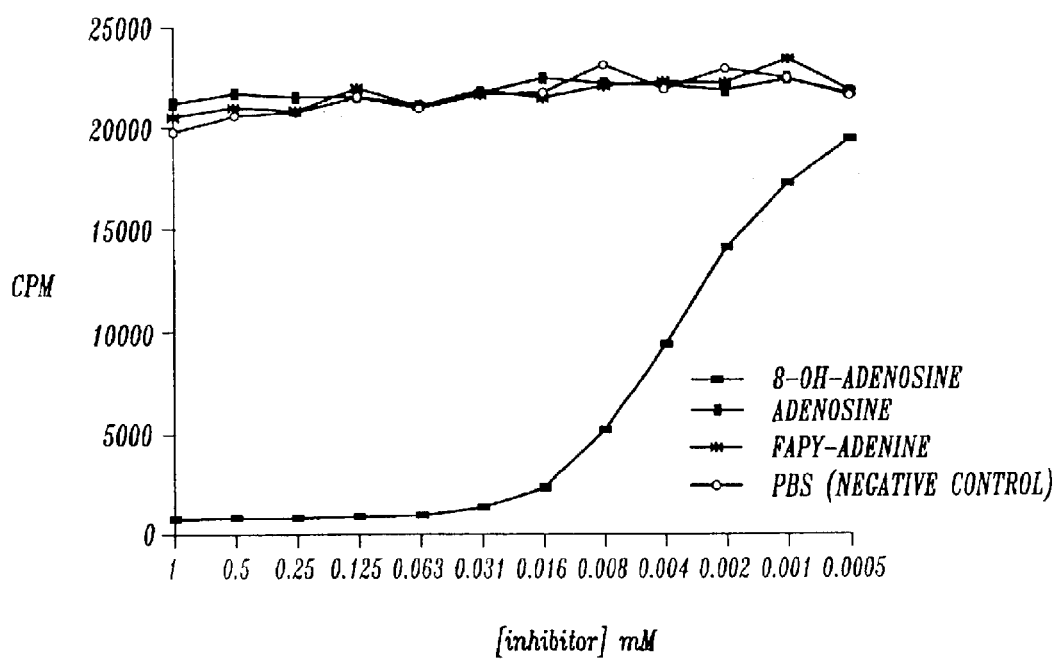
FIG. 20 is a graph showing inhibition of antibody binding to 8-OH-adenosine-BSA conjugates by soluble ligands for the monoclonal antibody 8A6 of the present invention. The data shows results of inhibition of antibody binding to 8-OH-adenosine conjugated BSA (50 µl of 50 µg of protein/ml as coating mixture) in a solid phase assay using commercial 8-OH-AMP (Sigma, St. Louis, Mo.) (prepared from 3',5'cyclic 8-OH-AMP after hydrolysis by nucleotidase), AMP, or4,6-diamino-5-formamidopyrimidine (Fapy-A) as shown in the FIGURE legend. The antibody present in culture supernatant was incubated in the presence of the indicated final concentration of soluble inhibitor overnight prior to the solid phase assay.
Figure 21:
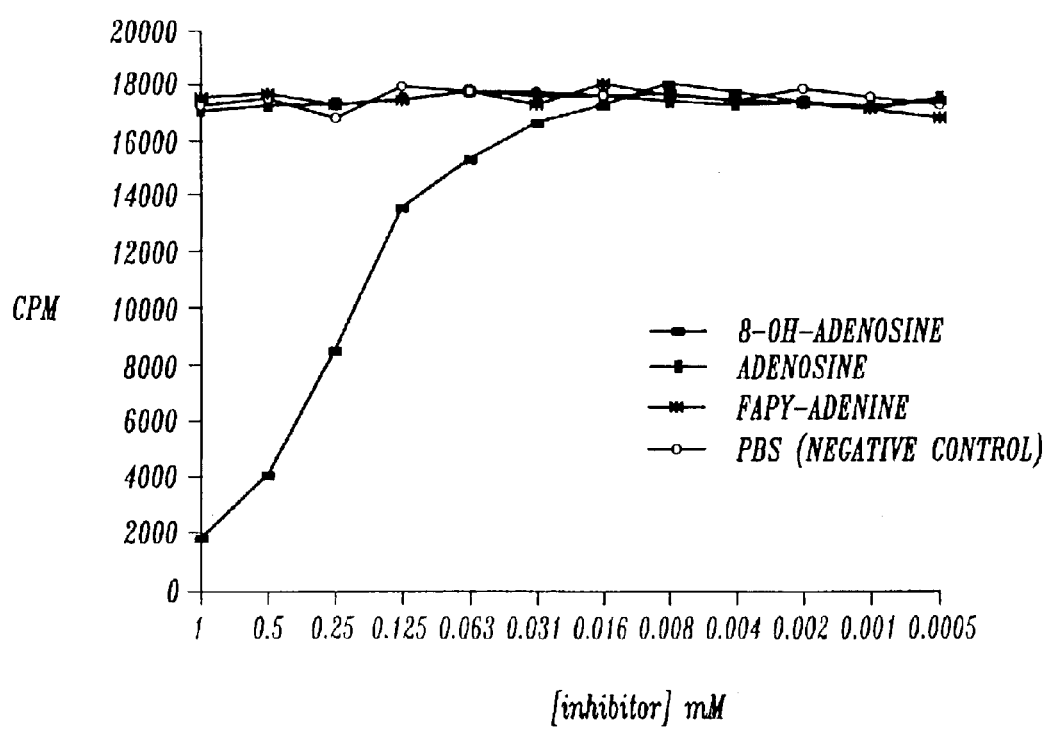
FIG. 21 is a graph showing inhibition of antibody binding to 8-OH-adenosine-BSA conjugates by soluble ligands for the monoclonal antibody 8A7 of the present invention. The data shows results of inhibition of antibody binding to 8-OH-adenosine conjugated BSA (50 µg of 50 µg of protein/ml as coating mixture) in a solid phase assay using commercial 8-OH-AMP (Sigma, St. Louis, Mo.) (prepared from 3',5'cyclic 8-OH-AMP after hydrolysis by nucleotidase), AMP, or4,6-diamino-5-formamidopyrimidine (Fapy-A) as shown in the FIGURE legend. The antibody present in culture supernatant, was incubated in the presence of the indicated final concentration of soluble inhibitor overnight prior to the solid phase assay.
Figure 22:
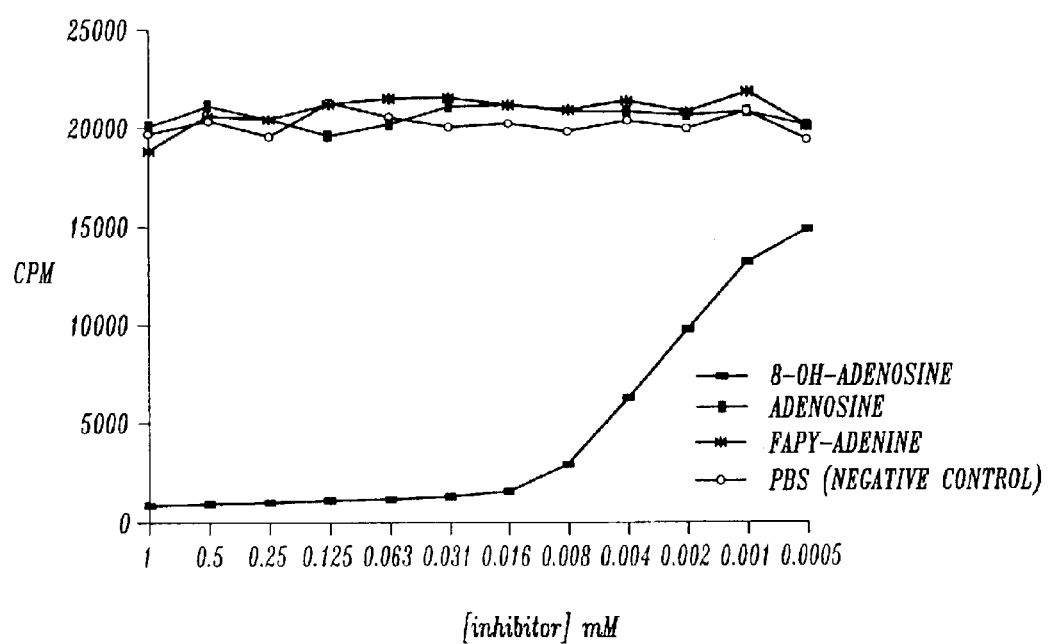
FIG. 22 is a graph showing inhibition of antibody binding to 8-OH-adenosine-BSA conjugates by soluble ligands or the monoclonal antibody 8A8 of the present invention. The data shows results of inhibition of antibody binding to 8-OH-adenosine conjugated BSA (50 µl of 50 µg of protein/ml as coating mixture) in a solid phase assay using commercial 8-OH-AMP (Sigma, St. Louis, Mo.) (prepared from 3',5'cyclic 8-OH-AMP after hydrolysis by nucleotidase), AMP, or, 4,6-diamino-5-formamidopyrimidine (Fapy-A) as shown in the FIGURE legend. The antibody present in culture supernatant was incubated in the presence of the indicated final concentration of soluble inhibitor overnight prior to the solid phase assay.
Figure 23:
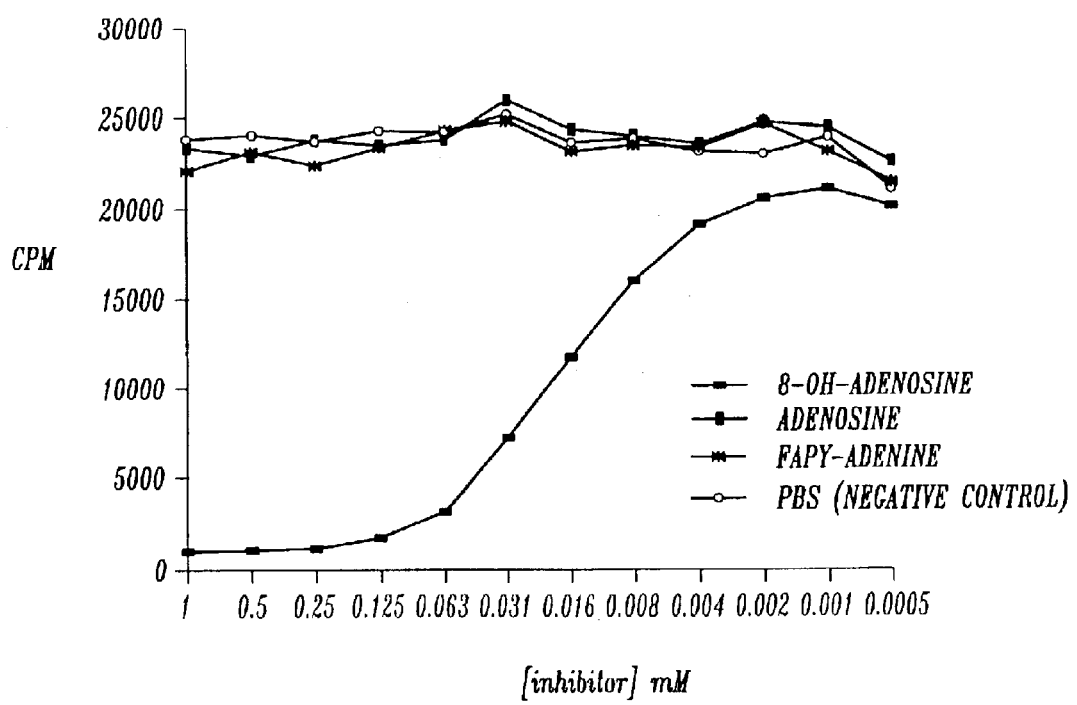
FIG. 23 is a graph inhibition of antibody binding to 8-OH-adenosine-BSA conjugates by soluble ligands for the monoclonal antibody 8A9 of the present invention. The data shows results of inhibition of antibody binding to 8-OH-adenosine conjugated BSA (50 µl of 50 µg of protein/ml as coating mixture) in a solid phase assay using commercial 8-OH-AMP (Sigma, St. Louis, Mo.) (prepared from 3',5'cyclic 8-OH-AMP after hydrolysis by nucleotidase), AMP, or 4,6-diamino-5-formamidopyrimidine (Fapy-A) as shown in the FIGURE legend. The antibody present in culture supernatant was incubated in the presence of the indicated final concentration of soluble inhibitor overnight prior to the solid phase assay.

Monoclonal antibodies of this invention can be prepared according to conventional methods by using 8-OH-adenosine conjugated to a carrier protein as an immunogen, as described in *Current Protocols in Immunology*, John Wiley & Sons, Inc. New York, N.Y. (1994), incorporated herein by reference. The synthesis of 8-OH-adenosine from 8-BR-adenosine is described in Cho et al., "Structure of Oxidatively Damaged Nucleic Acid Adducts. 3 Tautomerism, Ionization and Protonation of 8-Hydroxyadenosine Studied by $^{15}$NMR Spectroscopy," *Nucleic Acids Research*, Vol. 19, pp. 1041–1047 (1991), West et al. (1982) and in Example 1 herein. FIG. 1 shows results of GC-MS/SIM analysis of synthetic 8-OH-adenosine prepared in accordance with the method of the present invention after hydrolysis using 60% formic acid and trimethylsilation. The product elutes as a major peak with a retention time of 9.7 min. There are only minor additional peaks in the total ion chromatogram, indicating high purity of this material. The retention time and mass spectrum of the synthetic 8-OH-adenosine are indistinguishable from a pure standard 8-OH-Ade, and monoclonal antibodies against 8-OH-adenosine react virtually equivalently against 8-OH-Ade.

To prepare the immunogen the 8-OH-adenosine product can be readily coupled to carrier proteins through the available amino groups by methods known in the art, although other types of antigen carrying molecules may be used. In a preferred embodiment of the present invention, 8-OH-adenosine is coupled to keyhole limpet hemocyanin (KLH) by Schiff base formation with the lysine groups of KLH, followed by reduction with NaCNBH$_3$. KLH is a preferred conjugation protein for such a coupling reaction since it aids in-stimulating an immune response from attached ligands. Harlow et al., Antibodies, Cold Spring Harbor Laboratory (1988). Because of this, such an antigen is not useful for hybridoma screening. Other antigen carrier molecules which may be suitable for practicing the present invention include, but are not limited to BSA, ovalbumin, nucleic acids, lipids, carbohydrates, and naturally occurring biological conjugates such as glucuronic acid conjugates.

Immunization may be carried out according to conventional methods well known to those skilled in the art, such as by subcutaneously, intravenously or intraperitoneally injecting the 8-OH-adenosine conjugated to a carrier protein into an animal. More specifically, the immunogen may be diluted with PBS or physiological saline to a suitable concentration, and then injected into the animal, together with a suitable adjuvant if necessary. The immunogen should be injected several times (3 to 5 times) at an interval of 7 to 10 days with 50 to 100 µg of immunogen in 0.1 ml total volume until the total volume injected reaches 100 µl per animal. A conventional carrier may be used for the injection. Spleen cells isolated from the animal three days after the completion of the injection of the 8-OH-adenine conjugate are desirable for use as immune cells.

In a preferred embodiment to the present invention balb/c mice were injected subcutaneously in multiple sites with 8-OH-adenosine-KLH conjugate, prepared by mixing the immunogen with PBS and Freund's incomplete adjuvant followed by emulsification. The mice were immunized four times at ten day intervals with a total volume of 100 µl of immunogen per animal. Three days after fusion, spleen cells were then isolated for use as immune cells.

The transformed mammalian cells immuned by an 8-OH-adenosine conjugate are then fused with mammal plasmacytoma to produce hybridomas A clone recognizing 8-OH-adenosine is selected from the hybridomas and the target monoclonal antibody is then obtained from the clone. In the above process there are few limitations to the mammal cells to be transformed with the immune antigen. It is desired that the immune antigen be selected taking its compatibility with the mammal plasmacytoma be fused into consideration. Mice, rats, rabbits and the like are generally preferable for use.

Various known myeloma cells can be used as mammal plasmacytoma to be fused with the above immune cells. Such myeloma cells include, for example, p3 (pe/x63-Ag8) (*Nature*, 256:495–497 (1975)), P3-U1 (*Current Topics of Microbiology and Immunology*, 81:1–7 (1987)), NS-1 (*Eur. J. Immunol.*, 6:511–519 (1976)), MPC-11 (*Cell*, 8405–415 (1976)), PS2/0 (*Nature*, 276:269–270 (1978)), FO (*J. Immunol. Meth.*, 35:1–21 (1980)), x63, 6, 5, 3 (*J. Immunol.*, 123:1548–1550 (1979)), S194 (*J. Exp. Med*, 148:313–323 (1978)), and R210 (*Nature*, 277:131–133 (1979)) of rat, and the like. In a preferred embodiment of the present invention, mouse X63 myeloma cells are used.

The fusion of the immune cell and the plasmacytoma can be carried out in accordance with known methods, (see Harlow et al. (1988)) in the presence of a fusion accelerator and in a conventional nutritious medium. Conventional fusion accelerators, such as polyethylene glycol (PEG) and sendai virus (HVJ) can be used. Optionally, adjuvants such as dimethylsulfoxide and the like may be used in order to promote the efficiency of the fusion. A conventional fusion ratio of about 1–10 immune cells per one plasmacytoma may be used. As a medium for the fusion, any medium used for the cultivation of the plasmacytoma, such as PRMI 1640 medium and MEM medium, as well as other various media used for the cultivation of this type of cell, can be used. Serum obtained by removing serum complement from fetal calf serum (FCS) is a typical example of the type of medium that may be used.

The fusion is carried out by thoroughly mixing a prescribed amount of the immune cells with the plasmacytoma and blending this mixture with a medium to which about 30–60% (w/v) of a PEG (e.g., PEG with an average molecular weight of 1,000–6,000) solution which has been heated to about 37° C. in advance is added. The cultivation in the HAT medium is continued for a period sufficient for cells other than hybridoma (such as unfused cells) to die, usually for several days to several weeks. The hybridoma obtained is then subjected to a conventional limiting dilution method to detect the target cell lines producing the antibody of interest. In a preferred method of the present invention, the hybridoma is subjected to limited dilution cloning containing $8 \times 10^5$ mouse thymocytes as feeder cells per well. RPMI medium with 10% FCS and 1 mM pyrovate and 2 mM glutamine thymocytes were used as feeder cells both for original fusion and in subcloning.

The detection of the antibody-producing cell lines of the present invention may be carried out according to standard methods commonly used for the detection of antibodies, as described in the laboratory manual by Harlow et al. (1988) cited elsewhere herein, for example. Standard methods commonly used include the ELISA method, the plaque method, the spot method, the agglomeration reaction method, the Ouchterlony method, the radio immunoassay (RIA), and the like. Use of 8-OH-adenosine-conjugated BSA as an antigen for the detection is desirable.

In accordance with a preferred embodiment of the present invention, supernatant was tested for binding to 8-OH-adenosine conjugated BSA in a solid phase binding assay. The initial differential screening of the fusion was conducted with an 8-OH-adenosine-BSA conjugate versus an adenosine-BSA conjugate, along with BSA alone. Reactivity of 8-OH-adenosine selected clones from two independent fusions with alternate antigens was analyzed. The number of independent clones reactive with BSA coupled to one of three antigens is shown in Table II below:

TABLE II

| Initial Differential Screening of Antibodies | | | |
|---|---|---|---|
| Fusion # | 8-OH-adenosine/BSA | Adenosine/BSA | BSA Control |
| 1 | 23 | 0 | 0 |
| 2 | 38 | 0 | 0 |

As demonstrated, the 8-OH-adenosine hapten was highly immunogenic by virtue of the considerable number of positive specific wells obtained in both fusions.

Hybridomas that showed reactive antibodies were further analyzed for binding specificity by comparing the reactivity of BSA conjugates linked to 8-OH-adenosine, native base structure, alternate oxidative products, irrelevant bases and oxidized products and a negative control. In accordance with the present invention and methods known in the art, antibody-producing cell lines were screened to obtain those cell lines that generate antibody having binding specificity for 8-OH-adenosine. See Example 4 and FIGS. 2 to 12. Hybridomas producing target monoclonal antibodies of the invention can be cultivated over generations in conventional media and can be stored in liquid nitrogen.

Collection of monoclonal antibodies of the present invention from hybridomas of the invention can be performed by cultivating the hybridoma according to conventional methods and obtaining the monoclonal antibody as a supernatant, or by administering the hybridoma to a mammal with which the hybridoma is compatible, allowing the hybridoma to proliferate, and collecting the desired antibodies from the ascites fluid. The former method is adaptable to the production of high purity monoclonal antibody, and the latter to mass production of monoclonal antibody; Monoclonal antibodies thus obtained may be purified by means of salting, gel filtration, affinity chromatography, or in accordance with other methods.

The monoclonal antibodies of the present invention are identified in Table I above. The isotype of each monoclonal antibody was determined by an Isostrip assay (Boehringer-Mannheim, Indianapolis, Ind.). The results were as shown in Table III below:

TABLE III

| Antibody | Isotype |
| --- | --- |
| 8A1 | IgM |
| 8A2 | IgG1 |
| 8A3.E10 | IgG1 |
| 8A3.E11 | IgG1 |
| 8A4.B7 | IgG1 |
| 8A4.G10 | IgG1 |
| 8A5 | IgG1 |
| 8A6 | IgG1 |
| 8A7 | IgM |
| 8A8 | IgG1 |
| 8A9 | IgG1 |

The antibodies of the present invention can be used to detect and quantitate (by the use of a standard curve) the presence of 8-OH-adenine in biological specimens of DNA. Procedures for doing this would include immobilizing the DNA, denaturing it to disrupt the base-pairing scheme exposing the free base structures, and quantitating the amount of 8-OH-Ade present per amount of DNA in a quantitative immunoassay similar to those described below.

The presence of 8-OH-Ade in a biological sample can be analyzed at a high sensitivity and precision and with a high specificity in a simple manner by the use of monoclonal antibodies of the invention in conventional immunoassay formats, such as enzymatic immunoassays EIA), enzyme-linked immunosorbent assays (ELISA), radioimmunometric assays (RIA), immunoturbidimetric assays, or others known in the prior art. The lab manual by Harlow et al. (1988) discusses many of these methods. Because the monoclonal antibodies of the present invention react with 8-OH-Ade with specificity they are useful for the determination of 8-OH-Ade in clinical samples by immunoassay, thus enabling screening for various diseases and exposure to toxicants associated with elevated levels of 8-OH-Ade and associated with mutagenesis resulting from oxidative DNA damage. Thus, the present invention further provides immunoassay methods for determining the presence or amount of 8-OH-Ade in a biological fluid sample using the monoclonal antibodies of the invention. The assay comprises immunochemical reagents for forming an immunoreaction product whose presence or amount relates, either directly or indirectly, to the presence or amount of 8-OH-Ade in the sample. Those skilled in the art will appreciate that there are numerous well known clinical diagnostic procedures in which the immunochemical reagents of this invention can be used to form an immunoreaction product whose presence and/or amount relates to the presence and/or amount of 8-OH-Ade present in a sample. While exemplary assay methods are described herein, the invention is not so limited. Various heterogeneous and homogenous protocols, either competitive or noncompetitive, can be employed in performing an assay of this invention.

For example, the monoclonal antibodies of the present invention can be used in a direct solid phase immunoassay of antigen present in a biological specimen. DNA can be extracted from a tissue, cell or urine, for example, and subjected to a solid phase assay under conditions where the results with known amounts of DNA (e.g. by weight) are compared to a standard curve containing known amounts of antigen. This methodology could also be applied to impure DNA fractions or unfractionated biological specimens such as tissue, cells, or bodily fluid and the results normalized to another parameter such as protein concentration or nucleic acid using alternate means for determining the amount of nucleic acid present in the specimen (e.g. the amount of adenine present).

Furthermore, the monoclonal antibodies of the present invention can be used in a quantitative immunohistochemical analysis of cells and tissues. For example, cells or tissue sections can be immobilized on glass slides under conditions which denature the cellular DNA, such as heating or drying the specimen. Antibody analysis can be conducted with, for example, fluorescently labeled 8-OH-Ade specific antibodies under conditions where the fluorescence intensity of the stained sections is proportional to the amount of 8-OH-Ade present in the specimen. A similar assay was previously described for monoclonal antibodies reactive with other types of modified nucleotide bases by Matsuda et al. (1993).

Alternatively, the 8-OH-Ade specific antibodies can be immobilized and used to absorb or capture soluble antigen from known amounts of biological specimens such as cells, tissue, and fluids, including bodily fluids. This can be used as a concentration step prior to elution and a detection and quantitation step using other methodologies such as HPLC-ECM (Shigenaga et al. (1989)) or GC-MS/SIM (Malins et al. (1993)) procedures. In addition, a detection and quantitation step involving inhibition of antibody binding to antigen as discussed below could be applied.

Furthermore, soluble antigen present in known amounts of biological specimens, including bodily fluids, can be detected and quantitated either directly or after an initial concentration step by determining the amount of this material required to provide inhibition of antibody binding to immobilized antigen. In these procedures, the specimen would be combined with monoclonal antibody of the present invention and incubated for a period of time sufficient to allow antibody complexes to form with the soluble antigen. The resulting mixture would be incubated with immobilized antigen and the amount of antibody binding to the immobilized antigen determined. The concentration of antigen present in the specimen would be determined by comparison to the effect with known amounts of 8-OH-Ade containing soluble fractions in either single determinations or in serial dilutions of the specimen. The dilution state required to relieve the inhibition of binding to the immobilized antigen to a proscribed level would be proportional to the concentration of 8-OH-Ade present in the specimen.

In another illustrative embodiment, a double antibody or "sandwich" immunoassay format may be employed comprising the steps of (a) forming a first immunoreaction admixture by admixing a sample with a first antibody, e.g., a monoclonal antibody, wherein the antibody and 8-OH-Ade present in the sample are capable of forming a first immunoreaction product (the first antibody can be operatively linked to a solid matrix); (b) maintaining the first immunoreaction admixture so formed under biological assay conditions for a time period sufficient to form the first immunoreaction product (the first immunoreaction product can then be separated from the sample); (c) forming a second immunoreaction admixture by admixing the first immunoreaction product with a second antibody, monoclonal or polyclonal, which recognizes 8-OH-Ade; (d) maintaining the second immunoreaction admixture so formed under biological assay conditions for a period sufficient to form the second or "sandwich" immunoreaction product; and (e) determining the presence and, optionally, the amount of second immunoreaction product formed, and thereby the presence and, optionally, the amount of 8-OH-Ade in the sample. Preferably, the second antibody is labeled, preferably with an enzyme, and thus the second imnmunoreaction product formed will be a labeled product to facilitate determination of the second immunoreaction product.

In preferred double antibody assay methods, the amount of immunoreaction product determined is related to the amount of immunoreaction product similarly formed and determined using a standard sample in place of the biological sample wherein the standard sample contains a known amount of 8-OH-Ade in accordance with this invention. Alternatively, a synthetic secondary standard can be used.

It is also preferred that the second antibody be directed to a site on the 8-OH-Ade which is not the same as the site to which the first antibody is directed. For example, the first antibody can be directed to a site other than that which reacts with the monoclonal antibodies of the present invention.

In any of the illustrative assays, the biological sample can be provided as a known or unknown quantity of urine, semen, seminal fluid, saliva, tissue, blood, or a blood derived product such as serum or plasma. Samples for study of oxidative DNA damage generally come from two main sources: urinary excretions of oxidized nucleosides and bases from DNA isolated target tissue or cells, such as lymphocytes. First, the DNA in the specimen must be immobilized, and then denatured to disrupt the base pairing scheme, exposing the tree base structures. The amount of antibody used can be known or unknown. The admixture is maintained under biological assay conditions for a predetermined period of from about 1 hour to about 16 hours at a temperature of from about 4° C. to about 37° C., most preferably about 22° C.

Biological assay conditions are those that maintain the biological activity of the immunochemical reagents of this invention and the 8-OH-Ade. Those conditions can generally include a temperature range of from about 4° C. to about 37° C., a pH value range of from at least about 6.0 to about 8.0, with a preferred range of 7.0 to 7.4, and an ionic strength varying from about 50 mM to 500 mM. Upon routine experimentation, other biological assay conditions may be learned. Methods for optimizing such conditions are well known to those skilled in the art.

Another assay format that is may be used in practicing the present invention is the precipitation assay. In this embodiment, the process comprises formation of an immunoreaction admixture by admixing a DNA sample obtained from a biological specimen with a monoclonal antibody of the invention to yield a precipitous immunoreaction product. The antibody can be operatively linked to a solid particulate such as a microparticle or bead, such that when antibody-antigen cross-linking occurs, the particulate matter aggregates, indicating the presence of the target material.

Another method is immunoturbidimetry because of its adaptability to automatic analysis, enabling a large number of samples to be measured at one time. Specifically, an amount of 8-OH-Ade in a sample of DNA obtained from urine, blood, or the like can be determined by adding one or more of the monoclonal antibodies of the present invention to the sample for the reaction and by measuring changes in the absorbence before and after the reaction.

Many other types of assays within the scope of this invention will be readily apparent to those skilled in the art.

Furthermore, the monoclonal antibodies of the present invention may form part of a kit comprising the monoclonal antibody of the invention and a means for detecting an immunoreaction product comprising 8-OH-Ade and the monoclonal antibody. Instructions for use of a packaged immunochemical reagent are also typically included in such a kit.

As used herein, the term "packaged" can refer to the use of a solid matrix or material such as glass, plastic, paper, fiber, foil and the like capable of holding within fixed limits an antibody of this invention. Thus, for example, a package can be a glass vial used to contain monoclonal milligram quantities of antibody of the present invention, or it can be a microliter plate well to which microgram quantities of a contemplated antibody has been operatively affixed. Alternatively, a package could include antibody-coated microparticles entrapped within a porous membrane or embedded in a test strip or dipstick, etc. Alternatively, the antibody can be directly coated onto a membrane, test strip or dipstick, etc. which contacts the sample fluid. Many other possibilities exist and will be readily recognized by those skilled in this art.

Instructions for use typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing an antibody of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, peptide, or antibody molecule that is part of the present invention, or used separately, and those atoms or molecules can be used alone or in conjunction with additional reagents. Such labels are themselves well known in the diagnostic art.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-diethylamine-1-natpthalenesulfonyl chloride (DANSC), tetramethyl-rhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis," *Antibody As a Tool*, Marchalonis et al., Eds., John Wiley & Sons, Ltd., pp. 189–231 (1982).

The indicating group may also be an enzyme such as horseradish peroxidase (HRP), glucose oxidase, or the like. In such cases where the principle indicating group is an enzyme such as HRP or glucose oxidase, additional reagents are required to indicate that a receptor-ligand complex (immunoreacant) has formed. Such additional reagents for HRP include hydrogen peroxide and an oxidation dye precursor such as diaminobenzidine. An additional reagent useful with glucose oxidase is 2,2,-azino-di-(3-ethyl-benzthiazoline-G-sulfonic acid) (ABTS).

Radioactive elements are also useful labeling agents and may be used in practicing the present invention. An exemplary radiolabeling agent is a radioactive element that produces gamma ray emissions. Elements which themselves emit gamma rays, such as $1^{24}I$, $1^{25}I$, $1^{28}I$, $1^{32}I$ and $5^{1}Cr$ represent one class of gamma ray emission-producing radioactive element indicating groups. Particularly preferred is $1^{25}I$. Another group of useful labeling means are those elements such as $1^1C$, $1^8F$, $1^5O$ and $1^3N$ which themselves emit positrons. Also useful is a beta emitter, such as $1^{11}$indium or 3H.

The linking of labels, i.e., labeling of peptides and proteins, is well known in the art. For instance, monoclonal antibodies produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are also applicable. See, for example, Aurameas et al., *Scand. J Immunol.*, 8(7):7–23 (1978); Rodwell et al., Biotech., 3:889–894 (1984); and U.S. Pat. No. 4,493,795.

The diagnostic test kit can also include, preferably as a separate package, a "specific binding agent," which is a molecular entity capable of selectively binding an antibody of this invention or a complex containing such a species, but is not itself an antibody of this invention. Exemplary specific binding agents are second antibody molecules, complement, proteins or fragments thereof. Preferably the specific binding agent binds the antibody when it is present as part of a complex.

In preferred embodiments, the specific binding agent is labeled. However, when the diagnostic system includes a -specific binding agent that is not labeled, the agent is typically used as an amplifying means or reagent. In these embodiments, the labeled specific binding agent is capable of specifically binding the amplifying means when the amplifying means is bound to a complex.

The diagnostic kits of the present invention can be used in an "ELISA" format to detect the quantity of 8-OH-Ade in biological samples of DNA obtained from biological specimens such as cells, plasma, saliva, serum, semen, seminal fluid tissue, urine or blood. "ELISA" refers to an enzyme linked immunosorbent assay such as those discussed above, which employ an antibody or antigen bound to a solid phase and an enzyme-antigen or enzyme-antibody conjugate to detect and quantify the amount of an antigen present in a sample. A description of the ELISA technique is found in Harlow et al. (1988).

Thus, in preferred embodiments a monoclonal antibody with inherent specificity for 8-OH-Ade can be affixed to a solid matrix to form a solid support. A reagent is typically affixed to a solid matrix by adsorption from an aqueous medium, although other modes of affixation applicable to proteins and peptides well known to those skilled in the art can be used.

Useful solid matrices are also well known in the art. Such materials are water insoluble and include the cross-linked dextran available under the trademark SEPHADEX (Pharmacia Fine Chemicals, Piscataway, N.J.); agarose; polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The immunoreagents of any diagnostic system described herein can be provided in solution, as a liquid dispersion or as a substantially dry powder, e.g., in lyophilized form. Where the indicating means is an enzyme, the enzyme's substrate can also be provided in a separate package. A solid support such as the above-described microtiter plate and one or more buffers can also be included as separately packaged elements in the diagnostic assay systems of this invention.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

Thus, the monoclonal antibodies of the present invention may be used in a variety of immunoassays to detect and quantitate 8-OH-Ade in biological specimens. These assays may be useful for research, diagnosis of disease, prognosis and tracking of response to treatment. The following examples illustrate a preferred method for making the monoclonal antibodies of the present invention.

EXAMPLE 1

Preparation of 8-OH-adenosine

8-OH-adenosine was prepared according to the method previously described in Cho et al.(1991). 8-Br-Adenosine (14 mmol) (Sigma, St. Louis, Mo.) was dissolved in 40 ml of dry DMSO and added to a mixture containing sodium benzyloxide. This reagent was made by reacting 1 g of sodium metal with 35 ml of benzyl alcohol in 100 ml of DMSO. The reaction mixture was heated at.65° C. for 24 hours, cooled to room temperature, acidified with glacial acetic acid, and poured into 1 L of anhydrous ether. Preparation of 8-OH-adenosine is a single step reaction due to the acid labile nature of the initial C8-benzyloxylation product which yields 8-OH-adenosine directly. The precipitate was collected, dissolved in methanol, and absorbed onto 5 g of silica gel (Merck, Darmstadt, Germany). The solvent was removed on a rotary evaporator, and the residue applied to a 500 ml bed volume silica gel column in a solvent composed of $CHCl_3:CH_3OH$ (4:1). The column was eluted with this solvent and fractions were collected. The elution of products was monitored by thin layer chromatography and appropriate fractions pooled. The fractions which contained 8-OH-adenosine were identified after GC-MS/SIM analysis of the purified components using standard methodology as described in Malins et al. (1993). The product was recrystallized from water and yielded about 0.5 g of pure 8-OH-adenosine as a white powder.

EXAMPLE 2

Coupling of 8-OH-adenosine to Keyhole Limpet Hemocyanin (KLH) and Bovine Serum Albumin (BSA)

The 8-OH-adenosine product can be readily coupled to carrier proteins through available amino groups. Coupling of this hapten to carrier protein was conducted through the ribose moiety of the nucleoside after mild oxidization by $NaIO_4$ at pH 4.5 using a sodium phosphate buffer. The progress of the oxidation reaction was followed by the change in mobility of the UV-absorbing spots after thin layer chromatography on silica gel plates using a solvent system composed of $CHCl_3:CH_3OH$ (2:1). The oxidized product migrates as a faster moving spot on the chromatogram. This introduces vicinal aldehyde groups capable of forming Schiff bases with primary amines.

The antigen for immunization was prepared by Schiff base formation with lysine groups of keyhole limpet hemocyanin (KLH) followed by reduction with $NaCNBH_3$. the antigen for hybridoma screening was prepared by coupling the $IO_4^-$ oxidized derivative to BSA. This placed the specific ligand of interest on a molecule that was ideal for solid-phase immunoassays to be used in the hybridoma screening process.

Hapten conjugates of BSA using a variety of negative control nucleotide base structures were prepared using these same procedures with commercially available periodate oxidized nucleosides (Sigma, St. Louis, Mo.). Commercially obtained periodate oxidized nucleosides used were adenosine, cytosine, uracil, and guanosine. In addition, 8-OH-guanosine, which was prepared according to the method described by Cho et al., *Chem. Res. Toxicol.*, Vol. 3, pp. 445–452, (1990), was also periodate oxidized and coupled to BSA. All BSA conjugates containing approximately 15 hapten molecules per protein subunit.

EXAMPLE 3

Preparation of Anti-8-OH-Ade Antibodies

The methods employed were standard procedures as described in the laboratory manual Harlow et al. (1988). Balb/c mice were injected subcutaneously in multiple sites with 8-OH-adenosine conjugated keyhole limpet hemocyanin. The immunogen was prepared by mixing 2 mg of 8-OH-adenosine-KLH conjugate in 900 µl of phosphate buffered saline (PBS), 100 µl of 2 mg/ml MDP (N-acetylmuramy 1-L-alanyl-D-isoglutamine (Pierce, Rockford, Ill.), and 1 ml of Freund's incomplete adjuvant (Sigma, St. Louis, Mo.) followed by emulsification. The mice were immunized 4 times at 10 day intervals with 100 µl of immunogen, the last 3 days before fusion. Spleen cells were isolated and fused with mouse X63 myeloma cells.

EXAMPLE 4

Solid Phase Immunoassay

Once clones of hybridoma cells appeared after HAT selection, supernatant was tested for binding to 8-OH-adenosine conjugated BSA in a solid phase binding assay on 96-well Probind plates. Wells containing reactive antibodies were moved to 24-well plates and expanded for more detailed analysis of binding specificity. Each reactive antibody was tested for specificity in side-by-side comparison of reactivity with BSA conjugates linked to the specific antigen, native base structure, alternate oxidative products, irrelevant bases and oxidized products, and a negative control. Wells showing antibody of proper specificity were selected and cloned to yield monoclonal antibody producing cell lines.

The 8-OH-adenosine-conjugated BSA was deposited on 96-well Probind plates by coating each well with 50 µl of a solution containing 50 µg protein conjugate per ml of 50 mM sodium phosphate buffer, pH 7.5, 5 mM $MgCl_2$, 15 mM $NaN_3$ and incubated overnight. The plates were blocked with PBS containing 5%BSA for 2 hours, followed by incubation with antibody containing culture supernatant for 18 hours. The plates were then washed extensively with PBS, followed by incubation with 1:500 diluted rabbit anti-mouse whole Ig (ICN Immunobiologicals, Costa Mesa, Calif.) for 1 hour. The plates were again extensively washed with PBS and incubated with $1^{25}$I-protein A (90,000 cpm/well) for 1 hour. The plates were washed again with PBS and the amount of $1^{25}$I in each well was determined in a gamma counter.

FIGS. 2 through 12 show results of solid phase immunoassays using senior dilutions of nucleoside-BSA conjugates and cloned hybridoma culture supernatants as the antibody source. The results indicate that antibodies 8A1, 8A2, 8A3.E10, 8A3.E11, 8A4.B7, 8A4.G10, 8A6, and 8A9 of the present invention were absolutely specific for 8-OH-adenosine haptens coupled to BSA. No cross reactivity was observed with BSA conjugated to either adenosine, cytosine, uracil, guanosine, or 8-OH-guanosine. A broader specificity was observed with 8A5 (FIG. 8) in which substantial reactivity with 8-OH-guanosine was also observed, and with 8A7 (FIG. 10) and 8A8 (FIG. 11) which also reacted with guanosine and adenosine, and 8-OH-guanosine, respectively.

In experiments to titrate antigen reactivity, the conjugate protein was serially diluted in the above buffer alone. As shown in FIGS. 2 to 12, the antibodies were capable of detecting very low amounts of 8-OH-Ade. In particular, antibodies 8A1, 8A2, 8A6, 8A7, 8A8 and 8A9 were reactive with 8-OH-Ade levels present in quantities of less than 5 fmol per assay well.

EXAMPLE 5

Inhibition of Antibody Binding by Soluble Ligands

Culture supernatants containing hybridomas of known titer were mixed with soluble ligands which were serially diluted 1:2 in a 96-well plate starting with a concentration of 1 mM down to 5 µM and incubated overnight at 4° C. followed by incubation for 2 hours on an 8-OH-adenosine-BSA antigen coated plate (50 µl of 50 µg/ml protein conjugate). Conditions of the assay were otherwise the same as described in Example 4 above.

Figure 24:
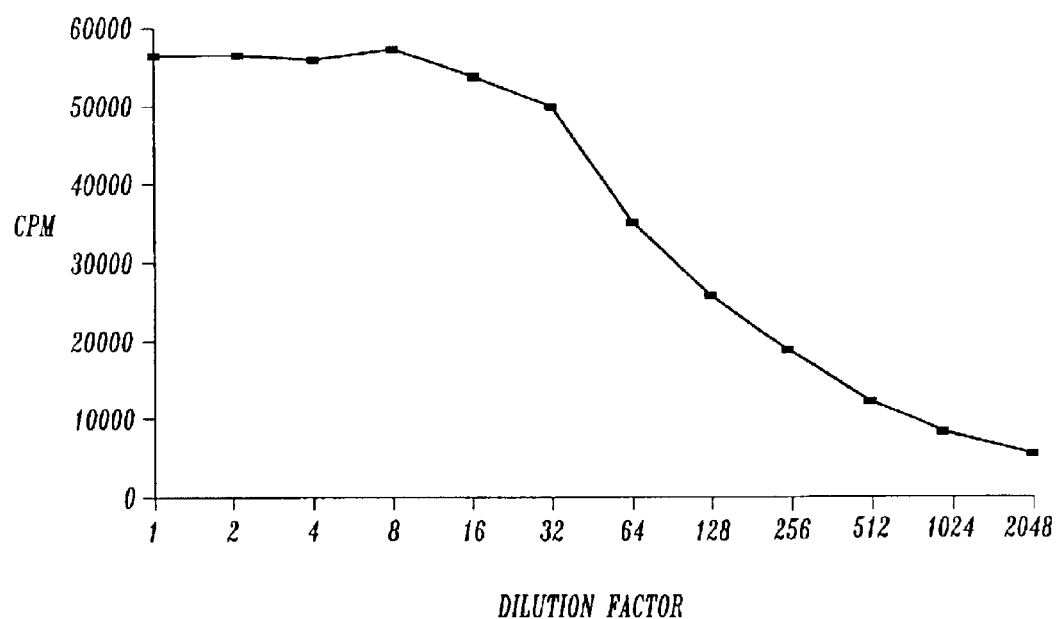
FIG. 24 is a sample antibody titration curve for determining dilution of antibody to be used in evaluating the ability of soluble ligands to inhibit antibody binding to immobilized 8-OH-adenosine conjugated BSA. The data shown is for antibody 8A2. The antibody dilution to be used based on this data was 1:32.

FIGS. 13 to 23 show results of inhibition of antibody binding to 8-OH-adenosine conjugated BSA (50 µg of protein/ml as coating mixture) in a solid phase assay using commercial 8-OH-AMP (Sigma, St. Louis, Mo.) (Prepared from 3',5'cyclic 8-OH-AMP after hydrolysis by nucleotidase), AMP, or 4,6-diamino-5-formamidopyridine (Fapy-A). Fapy-A is a ring-opening oxidation product from single electron oxidations and is an alternate reaction product of the same reaction which leads to 8-OH-adenosine. In these experiments the titer of antibody present in the culture supernatant used was adjusted to yield near maximal, but not saturating levels of antibody binding so that the antibody titer was not in large excess over the antigen coated onto the plate. This is demonstrated in FIG. 24. The results indicate that in the cases of antibodies 8A1, 8A2, 8A3.E10, 8A3.E11, 8A4.B7, 8A4.G10, 8A6, 8A7, 8A8, and 8A9 specific inhibition of antibody binding was observed only for 8-OH-AMP as its concentration was varied from 1 mM to 5 µM. No apparent inhibition with any antigen under the concentration range used was observed for 8A5. The concentration of soluble 8-OH-AMP capable of inhibiting the solid phase antibody binding was variable among the antibodies, with 8A6 and 8A9 showing the lowest concentrations of the soluble ligand capable of binding inhibition.

Figure 25:
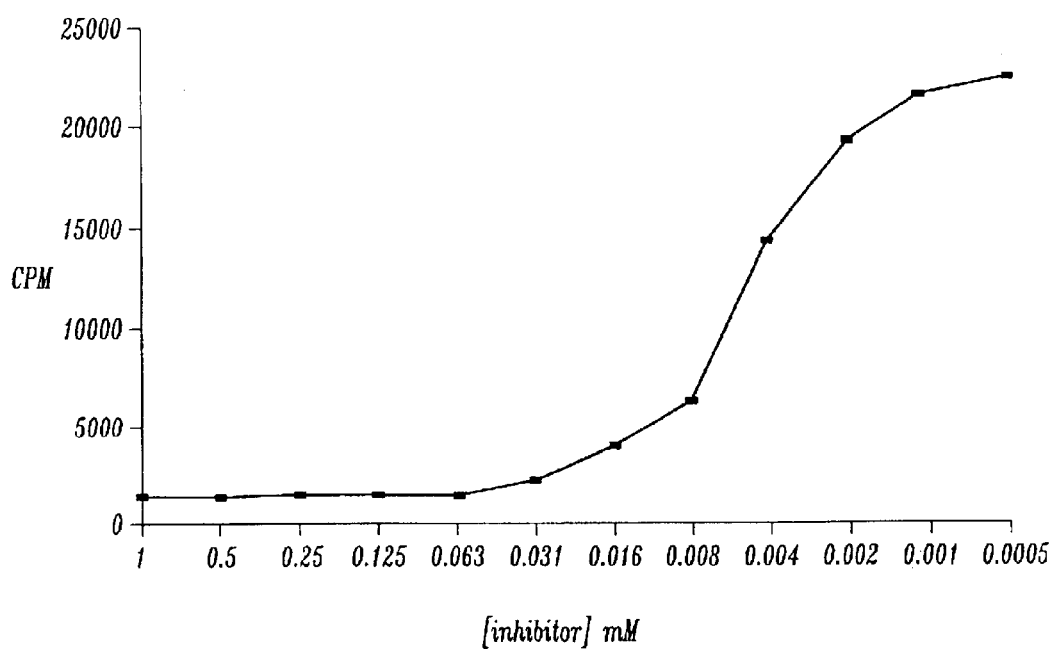
FIG. 25 is a graph showing inhibition of antibody binding to 8-OH-adenosine-BSA conjugates by soluble ligands for monoclonal antibody 8A6 of the present invention. The data shows results of inhibition of antibody binding to 8-OH-adenosine conjugated BSA (50 μl of 50 μg of protein/ml as coating mixture) in a solid phase assay using commercial 8-OH-AMP (Sigma, St. Louis, Mo.) (prepared from 3',5'cyclic 8-OH-AMP after hydrolysis by nucleotidase). The antibody present in culture supernatant was diluted 1:12 and incubated in the presence of the indicated final concentration of soluble inhibitor overnight prior to the solid phase assay.
Figure 26:
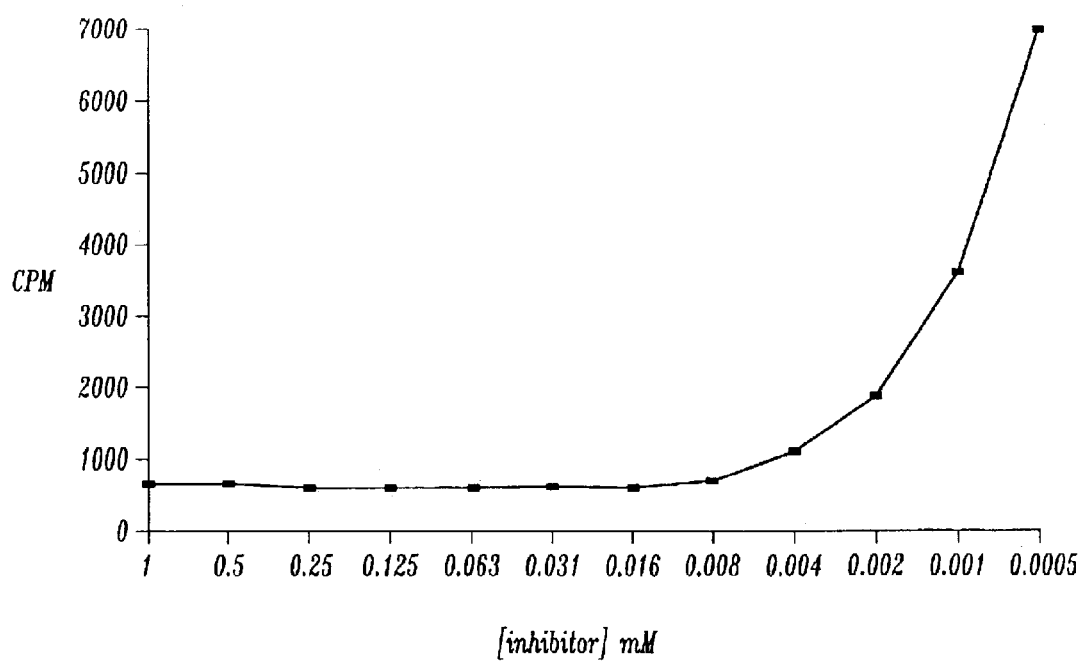
FIG. 26 is an inhibition of antibody binding to 8-OH-adenosine-BSA conjugates by soluble ligands for monoclonal antibody 8A6 of the present invention. The data shows results of inhibition of antibody binding to 8-OH-adenosine conjugated BSA (50 μl of 1.56 μg of protein/ml as coating mixture) in a solid phase assay using commercial 8-OH-AMP (Sigma, St. Louis, Mo.) (prepared from 3',5'cyclic 8-OH-AMP after hydrolysis by nucleotidase). The antibody present in culture supernatant was diluted 1:12 and incubated in the presence of the indicated final concentration of soluble inhibitor overnight prior to the solid phase assay.
Figure 27:
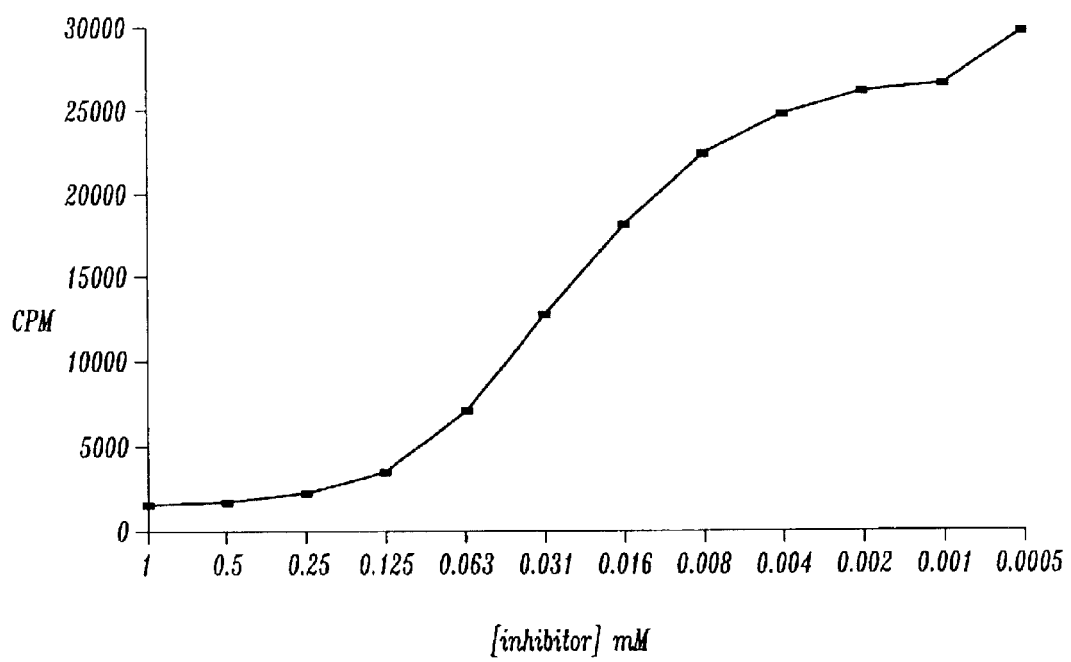
FIG. 27 is a graph showing inhibition of antibody binding to 8-OH-adenosine-BSA conjugates by soluble ligands for the monoclonal antibody 8A9 of the present invention. The data shows results of inhibition of antibody binding to 8-OH-adenosine conjugated BSA (50 μl of 50 μg of protein/ml as coating mixture) in a solid phase assay using commercial 8-OH-AMP (Sigma, St. Louis, Mo.) (prepared from 3',5'cyclic 8-OH-AMP after hydrolysis by nucleotidase). The antibody present in culture supernatant was diluted 1:25 and incubated in the presence of the indicated final concentration of soluble inhibitor overnight prior to the solid phase assay.
Figure 28:
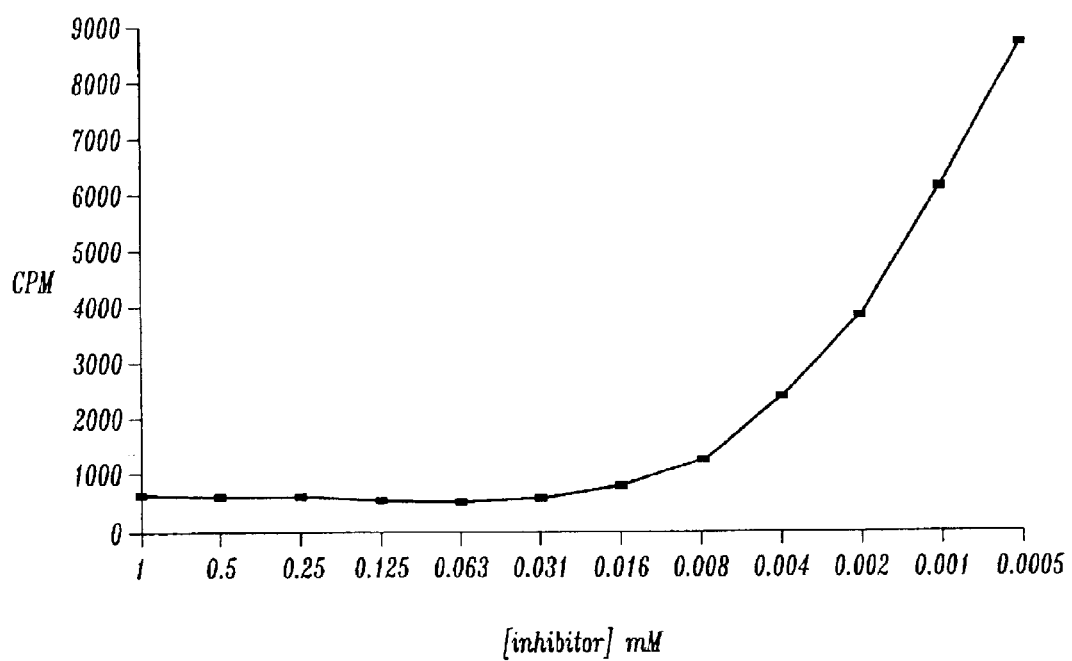
FIG. 28 is a graph showing inhibition of antibody binding to 8-OH-adenosine-BSA conjugates by soluble ligands by the monoclonal antibody 8A9 of the present invention. The data shows results of inhibition of antibody binding to 8-OH-adenosine conjugated BSA (50 μl of 0.78 μg of protein/ml as coating mixture) in a solid phase assay using commercial 8-OH-AMP (Sigma, St. Louis, Mo.) (prepared from 3',5'cyclic 8-OH-AMP after hydrolysis by nucleotidase). The antibody present in culture supernatant was diluted 1:25 and incubated in the presence of the indicated final concentration of soluble inhibitor overnight prior to the solid phase assay. The results are shown for antibody 8A9.

To determine if changes in experimental conditions can modulate the concentration of soluble ligand capable of causing significant binding inhibition, the ratio of soluble 8-OH-AMP ligand to immobilized 8-OH-adenosine present in BSA conjugates was varied and the effect on the concentration of soluble ligand capable of inhibiting antibody binding determined. The results for antibody 8A6 is shown in FIGS. 25 and 26. FIG. 25 shows results under standard conditions with plates coated with the BSA conjugate at a concentration of 50 µg/ml compared to an amount 32-fold lower shown in FIG. 26. These results indicate that this change in the ratio of soluble to bound ligand reduced the concentration of soluble ligand needed to provide a similar amount of binding inhibition by a factor of about 16. A similar study was also conducted with antibody 8A9 as shown in FIGS. 27 and 28 with more striking results. The concentration of soluble ligand capable of providing the same amount of inhibition in comparisons of the standard condition (50 μl of 50 μg/ml protein coated per well) versus a 64-fold dilution (i.e. 50 μl of 0.78 μg/ml protein) was itself 64-fold lower. Thus, the ratio of bound vs. soluble antigen in the inhibition assay can be adjusted to provide a more sensitive assay and the assay can be adjusted to detect binding inhibition caused by very low concentrations of soluble antigen. This is done by reducing the amount of bound antigen used in the assay and amplifying the signal due to primary antibody binding to it so that low concentrations of soluble antigen can effectively competitively bind to the antigen binding site on the antibody and result in detectable binding inhibition. Such an assay can be used to determine the presence and concentration of soluble antigen present in biological specimens and bodily fluids including, but not limited to, blood or urine.

EXAMPLE 6

Binding of Antibodies 8A6 and 8A9 to Physiological DNA Specimens

The ability of this panel of monoclonal antibodies to detect 8-OH-Ade lesions in physiological DNA was tested. For convenience, antibodies 8A6 and 8A9 were selected for this analysis. DNA specimens were analyzed for the levels of 8-OH-Ade present using GC-MS/SIM methodology (Malins et al. (1993)). Control DNA contained 1.2 8-OH-Ade lesions per $10^5$ normal bases. Test DNA contained 4.7 8-OH-Ade lesions per $10^5$ normal bases.

DNA specimens (50 ng) were dissolved in 100 μl of 1 M ammonium acetate and slot blotted onto nitrocellulose membrane (0.45 micron) using a Minifold II slot-blot system (Schleicher & Schuell, Keene, N.H.) according to manufacturer's instructions. The blots were removed and heated in an oven at 80° C. for 1 hour to denature the DNA. The blots were blocked using 25 mM Tris-HCl, pH 7.4, 150 mM NaCl, 0.1% Tween-20, 5% non-fat dry milk overnight at room temperature, followed by treatment with culture supernatants containing monoclonal antibody for 3 hours at room temperature. The blots were washed extensively with blocking buffer and followed by incubation with 1:1000 diluted rabbit anti-mouse whole Ig secondary antibody (ICN, Costa Mesa, Calif.) for 1 hour at room temperature. This antibody was diluted in blocking buffer without milk. After extensive washing with blocking buffer, the blots were incubated with $1^{25}$I-Protein (20,000 cpm per 50 μl) for 1 hour at room temperature. $1^{25}$I-Protein A was also diluted in blocking buffer without milk. After extensive washing with blocking buffer, the blots were dried and exposed to x-ray film overnight to visualize spots. The labeled spots were cut out and counted in a gamma counter. Net cpm $1^{25}$I-Protein A bound was calculated after subtraction of background. Background counts were determined by counting an equal area of the blot which contained no DNA.

TABLE IV

Analysis of Binding of Antibodies 8A6 and 8A9 to Denatured DNA Specimens of Known 8-OH-Ade Concentration

| DNA Specimen | # 8-OH-Ade $10^5$ bases | fmol 8-OH-Ade/ assay | Net cpm $^{125}$I-Protein A Bound | |
|---|---|---|---|---|
| | | | Antibody 8A6 | Antibody 8A9 |
| Control DNA | 1.2 | 0.5 | 882 | 910 |
| Test DNA | 4.7 | 1.8 | 3671 | 4602 |

The data obtained is shown in Table IV below. The amount of 8-OH-Ade present at each blot is shown, as is the net cpm of $1^{25}$I-Protein A bound. This value is proportional to the amount of 8A6 or 8A9 antibody bound to the DNA on the blot. This data shows increased antibody binding to test DNA compared to the control. In addition, each antibody is capable of producing a clear signal above background when 8-OH-Ade is present in the range of 2 fmol/assay. Thus, these data confirm that the antibodies bind directly to physiological DNA and are capable of detecting low fmol quantities of 8-OH-Ade per assay.

In summary, the present invention comprises a panel of highly specific monoclonal antibodies reactive with the modified nucleoside structure 8-OH-adenosine. The results of the inventors' experiments further define that it is the base portion of the structure (8-OH-Ade) and not the carbohydrate (ribose) or protein linkage region of the conjugate which is involved in antibody binding. This is known because conjugates with alternate nucleosides other than 8-OH-adenosine were unreactive with these antibodies, as demonstrated in Example 4 and FIGS. 2 to 12. In addition, direct binding of antibodies to 8-OH-Ade present in physiological DNA was demonstrated (see Example 6). In some instances minor specificities of certain antibodies were found (all of which correlate with antibody binding to the base structure). Of particular interest in this regard is antibody 8A5 which is reactive primarily with 8-OH-Ade but also detects 8-OH-guanosine. Also of interest are antibodies 8A7 and 8A8 which show some reactivity to guanosine. Thus, monoclonal antibody 8A5 in particular (or one similar to it), and antibodies 8A7 and 8A8 may be useful in detecting 8-OH-adducts of purines generally.

The results obtained by the inventors are typical for binding specificities of monoclonal antibodies. That is, specificity is defined by certain epitope portions of a larger molecule. Beyond the specific epitope, there is no recognition and no bias as to the chemical form containing the epitope for antigen presentation to the antibody. Similar results were demonstrated by the inventors for anticarbohydrate antibodies (Holmes and Greene, Arch. Biochem. Biophys., 288, 87–96, 1991). In those instances, the aglycone portion carrying the antigen (e.g. from lipid to protein) was demonstrated to be irrelevant and antibody binding independent from it.

The base ligand structure as the specific epitope for the antibodies of the present invention is further supported by antibody binding inhibition studies with soluble ligands. Soluble 8-OH-adenosine containing ligands specifically inhibited solid phase antibody binding, as demonstrated by the results shown in FIGS. 13 to 23. Soluble 8-OH-AMP (a single nucleotide moiety component of nucleic acids) inhibited antibody binding but adenine (from AMP) or Fapy-A structures did not. Thus, the antibodies of the present invention recognized antigen presented by both phosphorylated native nucleotides and periodate oxidized nucleosides. This last condition is suitable to cause ribose ring opening and, after reduction of a Schiff base with a protein amino group, yields a very different and non-physiological structure.

Given these results, the only possible conclusion is that the monoclonal antibodies of the present invention are specific for the base structure (8-OH-Ade) alone and are independent of the nature of the group or structure the base is coupled to. Therefore, these antibodies are useful in detecting and quantitating the amount of 8-OH-Ade present in biological specimens by virtue of their ability to specifically bind to this ligand.

The foregoing illustrative examples relate to the measurement of 8-OH-Ade in a biological sample using monoclonal antibodies. While the preferred embodiment of the present invention has been described in terms of specific conditions and format, it is understood that numerous variations and modifications will occur to those skilled in the art upon consideration of the present invention without departing from the spirit and scope of the invention.

The embodiments of the invention in which an exclusive property or privilege is claimed are defined as follows:

1. A monoclonal antibody having the specific binding characteristics of an antibody isolated from hybridoma ATCC HB12188 or ATCC HB12189, wherein the monoclonal antibody is specific for 8-hydroxyadenine and allows detection of the presence 8-hydroxyadenine in a binding assay comprising 50 ng of DNA, the DNA contains as few as 4.7 8-hydroxyadenine bases per $10^5$ bases.

2. The monoclonal antibody of claim 1, wherein the 8-hydroxyadenine is 8-hydroxyadenosine or 8-hydroxydeoxyadenosine and wherein the monoclonal antibody specifically binds to an epitope on the base portion of 8-hydroxyadenosine or 8-hydroxydeoxyadenosine and does not cross-react with other nucleotide bases nor with carbohydrate or protein portions of carbohydrate or protein conjugates of 8-hydroxyadenine or other nucleoside bases.

3. A hybridoma that produces the monoclonal antibody of claim 1.

4. A hybridoma that produces the monoclonal antibody of claim 2.

5. A monoclonal antibody having the specific binding characteristics of an antibody isolated from hybridoma ATCC HB12188 or ATCC HB12189, wherein the monoclonal antibody is specific for 8-hydroxyadenine and allows detection of the presence as little as 2 fmol of 8-hydroxyadenine.

6. The monoclonal antibody of claim 5, wherein the 8-hydroxyadenine is 8-hydroxyadenosine or 8-hydroxydeoxyadenosine and wherein the monoclonal antibody specifically binds to an epitope on the base portion of 8-hydroxyadenosine or 8-hydroxydeoxyadenosine and does not cross-react with other nucleotide bases nor with carbohydrate or protein portions of carbohydrate or protein conjugates of 8-hydroxyadenine or other nucleoside bases.

7. A hybridoma that produces the antibody of claim 5.

8. A hybridoma that produces the monoclonal antibody of claim 6.

* * * * *

UNITED STATES PATENT AND TRADEMARK OFFICE
CERTIFICATE OF CORRECTION

PATENT NO. : 6,900,291 B2
DATED : May 31, 2005
INVENTOR(S) : E.H. Holmes et al.

It is certified that error appears in the above-identified patent and that said Letters Patent is hereby corrected as shown below:

Title page,
Item [*] Notice, insert in appropriate order -- This patent is subject to a terminal disclaimer. --.
Item [56], References Cited, FOREIGN PATENT DOCUMENTS, delete as duplicative "WO 93/12258 6/1993"; and "WO 95/07907 3/1995".
OTHER PUBLICATIONS, "4710-4708.*" should read -- 4710-4718.* --; and "4762-4766.*" should read -- 472-476.* --.

Column 23,
Line 24, "DNA, the" should read -- DNA, wherein the --.

Column 24,
Line 24, "the antibody" should read -- the monoclonal antibody --.

Signed and Sealed this

Fourth Day of October , 2005

JON W. DUDAS
*Director of the United States Patent and Trademark Office*